(12) United States Patent
Cooper et al.

(10) Patent No.: US 7,064,126 B2
(45) Date of Patent: Jun. 20, 2006

(54) COMPOUNDS

(75) Inventors: Martin Edward Cooper, Loughborough (GB); Simon David Guile, Loughborough (GB); Anthony Howard Ingall, Loughborough (GB); Rukhsana Tasneem Rasul, Loughborough (GB)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 10/542,194

(22) PCT Filed: Jan. 15, 2004

(86) PCT No.: PCT/SE2004/000051

§ 371 (c)(1),
(2), (4) Date: Jul. 14, 2005

(87) PCT Pub. No.: WO2004/065393

PCT Pub. Date: Aug. 5, 2004

(65) Prior Publication Data

US 2006/0052380 A1    Mar. 9, 2006

(30) Foreign Application Priority Data

Jan. 17, 2003   (SE) .................................. 0300120

(51) Int. Cl.
C07D 495/04   (2006.01)
A61K 31/5025   (2006.01)

(52) U.S. Cl. ...................... 514/248; 544/235
(58) Field of Classification Search ................ 544/235; 514/248
See application file for complete search history.

(56) References Cited

U.S. PATENT DOCUMENTS 6,232,320 B1   5/2001   Stewart et al. .............. 514/301

FOREIGN PATENT DOCUMENTS

| WO | WO 98/54190 | 12/1998 |
| WO | WO 99/29695 | 6/1999 |
| WO | WO 00/12514 | 3/2000 |
| WO | WO 03/008422 | 1/2003 |
| WO | WO 03/011868 | 2/2003 |
| WO | WO 04/065394 | 8/2004 |
| WO | WO 04/065395 | 8/2004 |

OTHER PUBLICATIONS

Yamaguchi et al., "Novel Antiasthmatic Agents with Dual Activities of Thromboxane $A_2$ Synthetase Inhibition and Bronchodilation. V.[1])Thienopyridazinone Derivatives", *Chem. Pharm. Bull.* 43(2):236-240 (1995).

*Primary Examiner*—Kahsay Habte
(74) *Attorney, Agent, or Firm*—Fish & Richardson P.C.

(57) ABSTRACT

The invention relates to thienopyridazinones of formula (I): wherein: $R^1$ is $C_{1-6}$ alkyl, $C_{2-6}$ alkenyl or $C_{3-6}$ cycloalkyl which is optionally substituted by $C_{1-6}$ alkyl, each of the above being optionally substituted by one or more halogen atoms; $R^2$ is $C_{1-6}$ alkyl; $R^3$ is a group CO—G or $SO_2$—G where G is a 5- or 6-membered ring containing a nitrogen atom and a second heteroatom selected from oxygen and sulphur adjacent to the nitrogen, and optionally substituted by up to 3 groups selected from hydroxyl and $C_{1-4}$ alkyl; Q is $CR^5R^6$ where $R^5$ and $R^6$ are as defined in the specification; and $R^4$ is a 5- to 10-membered mono- or bi-cyclic aromatic ring system, containing 0 to 4 heteroatoms independently selected from nitrogen, oxygen and sulphur, the ring system being optionally substituted as described in the specification, and pharmaceutically acceptable salts and solvates thereof. Processes for their preparation, pharmaceutical compositions containing them and their use in therapy, in particular in the modulation of autoimmune disease are also described.

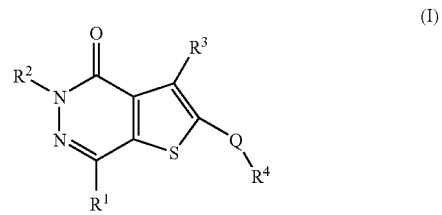

(I)

11 Claims, No Drawings

COMPOUNDS

CROSS-REFERENCE TO RELATED APPLICATIONS

This application is the National Stage of International Application No. PCT/SE2004/000051, filed Jan. 15, 2004, which claims the benefit of Swedish Patent Application Serial No. 0300120-3, filed Jan. 17, 2003. The contents of both prior applications are hereby incorporated by reference in their entireties.

The present invention relates to thienopyridazinones, processes for their preparation, pharmaceutical compositions containing them and their use in therapy. The invention also relates to their use in the modulation of autoimmune disease.

T-cells play an important role in the immune response, however in auto-immune disease T-cells are inappropriately activated against particular tissues and proliferate, eg causing the inflammation associated with rheumatoid arthritis. Inhibition of the proliferation of T-cells is beneficial in the modulation of autoimmune disease. The present invention relates to compounds which are beneficial in the modulation of autoimmune disease. In accordance with the present invention, there is provided a compound of formula (1):

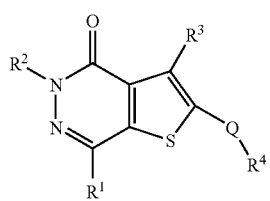

(1)

wherein:
$R^1$ is $C_{1-6}$ alkyl, $C_{2-6}$ alkenyl, $C_{1-6}$ alkyl-$C_{3-6}$ cycloalkyl or $C_{3-6}$ cycloalkyl which is optionally substituted by $C_{1-6}$ alkyl, each of these $R^1$ above being optionally substituted by one or more halogen atoms;
$R^2$ is $C_{1-6}$ alkyl;
$R^3$ is a group CO—G or $SO_2$—G where G is a 5- or 6-membered ring containing a nitrogen atom and a second heteroatom selected from oxygen and sulphur adjacent to the nitrogen, and optionally substituted by up to 3 groups selected from hydroxyl and $C_{1-4}$ alkyl;
Q is $CR^5R^6$ where $R^5$ is hydrogen, $C_{1-6}$ alkyl or fluorine and $R^6$ is hydrogen, OH or fluorine, or $R^5$ and R 6 together form a =O group, with the proviso that $R^5$ cannot be fluorine when $R^6$ is OH;
$R^4$ is a 5- to 10-membered mono- or bi-cyclic aromatic ring system, containing 0 to 4 heteroatoms independently selected from nitrogen, oxygen and sulphur, the ring system being optionally substituted by up to 4 groups independently selected from halogen, $C_{1-4}$ alkyl, (poly)halo-$C_{1-4}$-alkyl, $C_{1-4}$ alkoxy, (poly)halo-$C_{1-4}$-alkoxy, $C_{1-4}$ alkylsulphonyl, (poly)halo-$C_{1-}$-alkylsulphonyl, oxo, thioxo, cyano, hydroxymethyl, methylthio, —$NR^7R^8$, —CO—$NR^7R^8$, —$SO_2.NR^7R^8$, or a 5- to 6-membered aromatic ring system wherein up to 3 ring atoms may be heteroatoms independently selected from oxygen, sulphur and nitrogen, and which may itself be substituted by up to 4 groups selected from halogen, $C_{1-4}$ alkyl, (poly)halo-$C_{1-4}$-alkyl, $C_{1-4}$ alkoxy, (poly)halo-$C_{1-4}$-alkoxy, $C_{1-4}$ alkylsulphonyl, (poly)halo-$C_{1-4}$-alkylsulphonyl, oxo, thioxo, cyano, hydroxymethyl, methylthio, —$NR^7R^8$, —CO—$NR^7R^8$, —$SO_2$—$NR^7R^8$;

$R^7$ and $R^8$ are independently hydrogen, $C_{1-4}$ alkyl; or $R^7$ and $R^8$ together with the nitrogen atom to which they are attached may form a 5 to 7 membered saturated heterocyclic ring,
and pharmaceutically acceptable salts and solvates thereof.

Preferably $R^1$ is $C_{1-6}$ alkyl or $C_{3-6}$ cycloalkyl. For instance, $R^1$ is selected from ethyl, isobutyl, isopropyl or cyclopropyl. More preferably $R^1$ is isobutyl, isopropyl or cyclopropyl.

Suitably $R^2$ is $C_{1-3}$ alkyl, such as methyl or ethyl. Preferably $R^2$ is methyl.

Suitably G in group $R^3$ is a 5-membered ring containing an oxygen atom, such as an isoxazolidinyl ring. Preferably the ring G is substituted by a single hydroxy substituent. A hydroxyl substituent may not be attached to a ring carbon atom that is bonded to a ring heteroatom. The group G is preferably linked to the CO or $SO_2$ group through its ring nitrogen atom. Particular examples of the group G are is 4-hydroxy-isoxazolidin-2-yl or 4-hydroxymethyl-isoxazolidin-2-yl.

Preferably $R^3$ is a group CO-G as defined above in which the ring G is linked via a nitrogen atom. More preferably $R^3$ is a group CO-G where G is a 5-membered ring as described above.

Most preferably $R^3$ is 4-hydroxy-isoxazolidin-2-ylcarbonyl or 4-hydroxy-4-methyl-isoxazolidin-2-yl carbonyl. Suitably Q is $CR^5R^6$ where $R^1$ is hydrogen, $C_{1-6}$ alkyl and $R^6$ is hydrogen. Preferably Q is $CH_2$.

Examples of 5–10 membered mono- or bi-cyclic aromatic ring systems for $R^4$ include thienyl, furanyl, pyrrolyl, pyrrolopyridino, imidazolyl, pyridyl, pyrazinyl, pyrimidyl, pyridazinyl, triazinyl, oxazolyl, thiazolyl, isoxazolyl, pyrazolyl oxadiazolyl, thiadiazolyl, triazolyl, tetrazolyl and quinolyl.

Where $R^4$ is a bicyclic aromatic ring system, a particular example is pyrrolopyridino Preferably $R^4$ is a 5-membered aromatic ring containing two heteroatoms optionally substituted as defined above. A particular example of $R^4$ is an optionally substituted pyrazole ring, Preferably $R^4$ is a substituted pyrazole ring Suitable substituents are those listed above, but in particular are selected from $C_{1-6}$alkyl, or halo $C_{1-6}$allyl or a 5- to 6-membered aromatic ring system wherein up to 3 ring atoms may be heteroatoms independently selected from oxygen, sulphur and nitrogen.

For instance, $R^4$ is suitably a group of sub-formula (i)

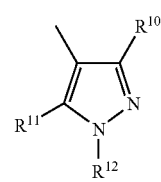

(i)

where $R^{10}$ and $R^{11}$ are independently selected from H, $C_{1-6}$alkyl, or halo$C_{1-6}$alkyl and $R^{12}$ is selected from H, $C_{1-6}$alkyl, or halo$C_{1-6}$alkyl or a 5- to 6-membered aromatic ring system wherein up to 3 ring atoms may be heteroatoms independently selected from oxygen, sulphur and nitrogen.

In $R^{10}$ and $R^{11}$ are selected from H or $C_{1-3}$alkyl, such as methyl. In particular, both $R^{10}$ and $R^{11}$ is $C_{1-3}$alkyl such as methyl.

Suitably $R^{12}$ is selected from H, $C_{1-3}$alkyl (such as methyl) or a 5- to 6-membered aromatic ring system wherein up to 3 ring atoms may be heteroatoms independently selected from oxygen, sulphur and nitrogen. Where $R^{12}$ is a 5- to 6-membered aromatic ring system, particular examples of such systems are pyridyl (such as 2-pyridyl), pyrimidinyl (such as 2-pyrimidinyl) or thiazolyl (such as 2-thiazolyl).

Preferably $R^{12}$ is H.

In an embodiment of the invention $R^4$ is a pyrazole ring, substituted by alkyl such as $C_{1-6}$alkyl, or halo$C_{1-6}$alkyl such as or trifluoromethyl substituents and/or also substituted by a 2-pyrimidinyl or 2-pyridyl group.

Where $R^7$ and $R^5$ form a 5 to 7 membered saturated heterocyclic ring examples of suitable rings include morpholine, piperidine, piperazine and pyrrolidine.

Preferred compounds of formula (I) include:

2-[(3,5-dimethyl-1H-pyrazol-4-yl)methyl]-3-[[(4S)-4-hydroxy-2-isoxazolidinyl]carbonyl-5-methyl-7-(1-methylethyl)thieno[2,3-d]pyridazin-4(5H)-one, 2-[(3,5-Dimethyl-1H-pyrazol-4-yl)methyl]-3-[[(4S)-4-hydroxy-2-isoxazolidinyl]carbonyl-5-methyl-7-(2-methylpropyl)thieno[2,3-d]pyridazin-4(5H)-one, 2-[(3,5-dimethyl-1H-pyrazol-4-yl)methyl]-7-ethyl-3-[[(4S)-4-hydroxy-2-isoxazolidinyl]carbonyl]-5-methyl-thieno[2,3-d]pyridazin-4(5H)-one, 7-Cyclopropyl-2[(3,5-dimethyl-1H-pyrazol-4-yl)methyl]-3-[[(4S)-4-hydroxy-2-isoxazolidinyl]carbonyl]-5-methyl-thieno[2,3-d]pyridazin-4(5H)-one, 7-Cyclopropyl-2-[(3,5-dimethyl-1H-pyrazol-4-yl)methyl]-5-ethyl-3-[[(4S)-4-hydroxy-2-isoxazolidinyl]carbonyl]-thieno[2,3-d]pyridazin-4(5H)-one, 2-[(3,5-Dimethyl-1H-pyrazol-4-yl)methyl]-3-[[(4S)-4-methyl-2-isoxazolidinyl]carbonyl-5-methyl-7-(1-methylethyl)thieno[2,3-d]pyridazin-4(5H)-one, 2-[(3,5-Dimethyl-1H-pyrazol-4-yl)methyl]-3-[[(4S)-4-hydroxy-4-methyl-2-isoxazolidinyl]carbonyl]-5-methyl-7-(2-methylpropyl)-thieno[2,3,-d]pyridazin-4(5H)-one, 2-[(3,5-Dimethyl-1H-pyrazol-40yl)methyl]-7-ethyl-3-[[(4S)-4-hydroxy-4-methyl-2-isoxazolidinyl]carbonyl]-5-methyl-thieno[2,3-d]pyridazin-4(5H)-one, 7-Cyclopropyl-2[(3,5-dimethyl-1H-pyrazol-4-yl)methyl]3-[[(4S)-4-hydroxy-4-methyl-2-isoxazolidinyl]carbonyl]-5-methyl-thieno[2,3-d]pyridazin-4(5H) one, 3-[[(4S)-4-hydroxyisoxazolidinyl]carbonyl]-5-methyl-7-(2-methylpropyl)-2-(1H-pyrrolo[2,3-b]pyridine-3-ylmethyl)thieno(2,3,-d]pyridazin-4(5H)-one, 3-[[(4S)-4-Hydroxy-2-isoxazolidinyl]carbonyl]-5-methyl-7-(2-methylpropyl)-2-[(1,3,5-trimethylpyrazol-4-yl)methyl]-thieno[2,3,-d]pyridazin-4(5H)-one, 2-[[3,5-dimethyl-1-(2-pyridinyl)-1H-pyrazol-4-yl]methyl]-7-ethyl-3-[[(4S)-4-hydroxy-2-isoxazolidinyl]carbonyl]-5-methyl-thieno[2,3-d]pyridazin-4(5H)-one, 2-[(3,5-Dimethyl-1-(2-pyridinyl)-1H-pyrazol-4-yl]methyl]-7-ethyl-3-[[(4S)-4-hydroxy-4-methyl-2-isoxazolidinyl]carbonyl]-5-methyl-thieno[2,3-d]pyridazin-4(5H)-one, 7-Ethyl-3-{[(4S)-4-hydroxy-4-methylisoxazolidin-2-yl]carbonyl}-5-methyl-2-(1H-pyrrolo[2,3-b]pyridin-3-ylmethyl)thieno[2,3-d]pyridazin-4(5H)-one, 2-[(3,5-Dimethyl-1-(2-pyridinyl)-1H-pyrazol-4-yl)methyl]-3-[[(4S)4-hydroxy-4-methyl-2-isoxazolidinyl]carbonyl-5-methyl-7-(1-methylethyl)thieno[2,3,-d]pyridazin-4(5H)-one, 2-[(3,5-Dimethyl-1-(2-pyrimidinyl)1H-pyrazol-4-yl)methyl]-3-[[(4S)-4-hydroxy-4-methyl-2-isoxazolidinyl]carbonyl-5-methyl-7-(1-methylethyl)thieno[2,3,-d]pyridazin-4(5H)-one, 2-[(3,5-Dimethyl-1-(2-thiazolyl)-1H-pyrazol-4-yl)methyl]-3-[[(4S)-4-hydroxy-4-methyl-2-isoxazolidinyl]carbonyl-5-methyl-7-(1-methylethyl)thieno[2,3,-d]pyridazin-4(5H)-one and pharmaceutically acceptable salts thereof.

Alkyl groups, whether alone or as part of another group, can be straight chained or branched. Unless otherwise specified, they will generally comprise from 1 to 6 and suitably from 1 to 4 carbon atoms.

Examples of (poly)halo$C_{1-4}$alkyl groups include halo$C_{1-4}$alkyl groups such as chloro- or fluoromethyl, as well as dihalo$C_{1-4}$alkyl groups such as difluoro- or dichloromethyl and trihalo$C_{1-4}$-alkyl groups such as trifluoromethyl.

It will be understood that a compound of the formula I or a salt thereof may exhibit the phenomenon of tautomerism and that the drawings within this specification represent only one of the possible tautomeric forms. It is to be understood that the invention encompasses any tautomeric form.

Certain compounds of formula (I) are capable of existing in stereoisomeric forms. It will be understood that the invention encompasses all geometric and optical isomers of the compounds of formula (I) and mixtures thereof including racemates. These also form an aspect of the present invention.

Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates and tartrates. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

Preferred salts include an acid addition salt such as a hydrochloride, hydrobromide, phosphate, acetate, fumarate, maleate, tartrate, citrate, oxalate, methanesulfonate or p-toluenesulfonate, or an alkali metal salt such as a sodium or potassium salt.

In a further aspect the invention provides a process for the preparation of a compound of formula (I) which comprises:

(a) for compounds of formula (I) where $R^3$ is COG: reaction of a compound of formula (II):

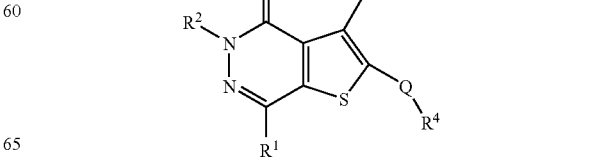

in which R¹, R², R⁴ and Q are as defined in formula (I) or are protected derivatives thereof, with a compound of formula (III):

G—H     (III)

where G is as defined in formula (I) in the presence of a coupling agent, or (b) for compounds of formula (I) where R³ is SO₂—G: reacting a compound of formula (IV):

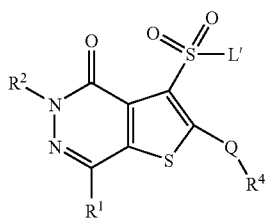

(IV)

in which in which R¹, R², R⁴ and Q are as defined in formula (II) and L and L' are leaving groups with a compound of formula (III) as defined above, and optionally thereafter
process (a) or (b) in any order
removing any protecting groups
forming a pharmaceutically acceptable salt.

When the compound of formula (III) is an nitrogen atom bonded to the H group, a preferred compound of formula (II) has hydroxy as the leaving group L, so that the reaction can be effected using amide coupling. Reaction of compounds (II) and (III) is suitable carried out in the presence of a coupling agent such as diethyl chlorophosphate and N-hydroxybenzotriazole and a base such as an organic amine, for example triethylamine. The reaction is carried out in a suitable solvent such as dichloromethane or acetonitrile at at temperature of about 0° C. to about 35° C., preferably at about 15° C. to about 25° C.

Suitable leaving groups L and L' include halo groups such as fluoro, chloro or bromo or in the case of the compound of formula (IV), it may be an anhydride group such as a sulphonic acid anhydride or acetyl anhydride.

Compounds of formula (II) can be prepared by reacting a compound of formula (V):

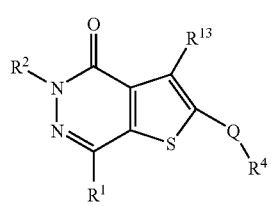

(V)

in which R¹, R², R⁴ and Q are as defined in formula (I), and R¹³ is a halo group such as bromo or iodo, and preferably bromo, with a suitable Grignard reagent followed by treatment with carbon dioxide. The reaction is preferably carried out using a hindered Grignard reagent such as isopropyl magnesium chloride in a solvent such as THF at reduced temperature, for example at about 0° C. to about 25° C., preferably at about 0° C. to about 5° C. with the carbon dioxide quench carried out at from about 0° C. to about 25° C.

Compounds of formula (V) where Q is CHR⁵ can be prepared by reacting a compound of formula (VI):

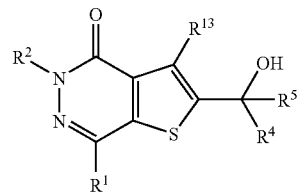

(VI)

in which R¹, R², R⁴ and Q are as defined in formula (II), and R¹³ is as defined in relation to formula (V), with a strong acid such as trifluoroacetic acid in the presence of a hydride source such as triethylsilane. The reaction is carried out optionally in the presence of a halocarbon solvent such as dichloromethane at a temperature of about 0° C. to about 35° C., preferably at about 15° C. to about 25° C.

Compounds of formula (VI) can be prepared by reacting a compound of formula (VII):

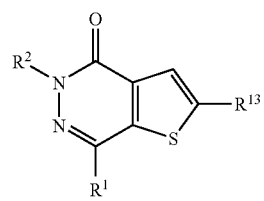

(VII)

in which R¹ and R² are as defined in formula (II) and R¹³ is as defined in relation to formula (V), with a lithium alkylamide such as lithium diisopropylamide in an aprotic solvent such as THF. The reaction is carried out at a temperature of between about –10° C. and about 25° C., preferably at about 0° C. to about 5° C., followed by treatment with a compound of formula (VIII):

R⁴—CO—R⁵     (VIII)

where R⁴ and R⁵ are as defined in formula (I) or are protected derivatives thereof, at a temperature of between about 0° C. and about 50° C., preferably at about 10° C. to about 30° C.

Compounds of formula (VII) can be prepared by treating a compound of formula (IX):

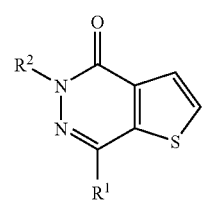

(IX)

in which R¹ and R² are as defined in formula (II) with a halogenating agent such as bromine, in an inert solvent such as aqueous acetic acid at a temperature of between about 20° C. and about 100° C., preferably at about 50° C. to about 100° C.

Compounds of formula (IX) can be prepared by reation of a compound of formula (X):

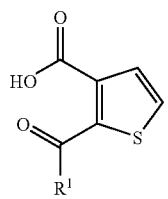

(X)

in which $R^1$ is as defined in formula (II) with a compound of formula (XI):

(XI)

in which $R^2$ is as defined in formula (11). The reaction can be carried out in a polar solvent such as ethanol at a temperature of about 20° C. to about 125° C., preferably at about 50° C. to about 100° C.

Compounds of formula (X) can be prepared by treating thiophene-3-carboxylic acid with a base, preferably a lithium alkylamide such as lithium diisopropylamide. The reaction is carried out in an aprotic solvent such as THF at a temperature of about −78° C. to about 25° C., preferably at about −50° C. to about 110° C. The anion is treated with a compound of formula (XII):

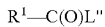

(XII)

in which $R^1$ is as defined in formula (II) and L″ is a leaving group such as O,N-dimethyl hydroxylamino, at a temperature of about 0° C. to about 50° C., preferably at about 10° C. to about 30° C.

Compounds of formula (IV) can be prepared from compounds of formula (V) by treating with a Grignard reagent as defined above and quenching with sulphur dioxide at a temperature of about −50° C. to about 100° C., followed by oxidation of the resulting intermediate and chlorination, for example with phosphorous pentachloride.

Compounds of formula (V) where Q is $CF_2$, that is a compound of formula (XIII):

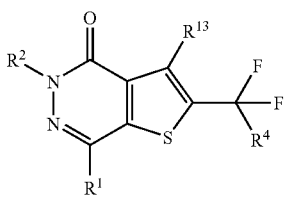

(XIII)

in which $R^1$, $R^2$ and $R^4$ are as defined in formula (II) and $R^{13}$ is as defined in relation to formula (V), can be prepared from a compound of formula (XIV):

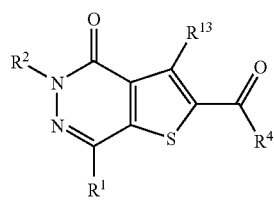

(XIV)

in which $R^1$, $R^2$ and $R^4$ are as defined in formula (II) and $R^{13}$ is as defined in relation to formula (V), by treating with a fluorinating agent such as diethylamino sulphur trifluoride in an inert solvent such as dichloromethane at a temperature from about −30° C. to about 50° C.

Compounds of formula (XIV) are prepared from compounds of formula (VI) as defined above where $R^5$ is hydrogen using an oxidant such as tetrapropylammonium perruthenate in the presence of N-methyl morpholine N-oxide in a solvent such as dichloromethane at a temperature of about −20° C. to about 50° C.

Starting materials as defined above are available commercially or can be prepared using routine chemistry known in the art.

Alternatively or additionally, compounds of formula (I) can be converted to different compounds of formula (I) using conventional chemical methods. For instance, compounds of formula (I) where $R^4$ is a group of sub-formula (i) above, wherein $R^{12}$ is hydrogen can be converted to compounds of formula (i) where $R^{12}$ is other than hydrogen by reaction with a compound of formula (XV)

(XV)

where $R^{12'}$ is a group $R^{12}$ other than hydrogen, and L‴ is a leaving group such as halo, and in particular bromo. Such a reaction may be carried out in an organic solvent such as acetonitrile or dioxan. If necessary the reaction can be carried out in the presence of a base such as an alkali metal carbonate, for instance potassium carbonate, and in the presence of a catalyst such as a copper salt like copper iodide. Also if necessary, the reaction can be effected under an inert atmosphere such as nitrogen.

Other reactions, in particular for the conversion of one group $R^3$ of $R^4$ to different such groups would be apparent to a skilled chemist.

The compounds of the invention are useful because they possess pharmacological activity in human and non-human animals. They are indicated as pharmaceuticals for use in the (prophylactic) treatment of autoimmune, inflammatory, proliferative and hyperproliferative diseases and immunologically mediated diseases including rejection of transplanted organs or tissues and Acquired Immunodeficiency Syndrome (AIDS).

Examples of these Conditions are:

(1) (the respiratory tract) airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamnentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Beheet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired mnmunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease; and (7) cancer.

Accordingly, the present invention provides a compound of formula (1) or a pharmaceutically acceptable salt thereof as hereinbefore defined for use in therapy.

In another aspect, the invention provides the use of a compound of formula (2) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of effecting immunosuppression (e.g. in the treatment of allograft rejection) which comprises administering to a patient a therapeutically effective amount of a compound of formula (1) or a pharmaceutically acceptable salt thereof as hereinbefore defined.

The invention still further provides a method of treating, or reducing the risk of, an airways disease (e.g. asthma or COPD) in a patient suffering from, or at risk of, said disease, which comprises administering to the patient a therapeutically effective amount of a compound of formula (1) or a pharmaceutically-acceptable salt thereof as hereinbefore defined.

For the above-mentioned therapeutic uses the dosage administered will, of course, vary with the compound employed, the mode of administration, the treatment desired and the disorder indicated. However, in general, for effecting immunosuppression, the daily dosage of the compound of formula (1) will be in the range from 0.1 mg/kg, preferably from 0.3 mg/kg, more preferably from 0.5 mg/kg and still more preferably from 1 mg/kg up to and including 30 mg/kg. For the treatment of airways diseases, the daily dosage of the compound of formula (I) will typically be in the range from 0.001 mg/kg to 30 mg/kg.

The compounds of formula (1) and pharmaceutically-acceptable salts thereof may be used on their own but will generally be administered in the form of a pharmaceutical composition in which the formula (1) compound/salt/solvate (active ingredient) is in association with a pharmaceutically-acceptable adjuvant, diluent or carrier. Depending on the mode of administration, the pharmaceutical composition will preferably comprise from 0.05 to 99% w (percent by weight), more preferably less than 80% w, e.g. from 0.10 to 70% w, and even more preferably less than 50% w, of active ingredient, all percentages by weight being based on total composition.

Thus, the present invention also provides a pharmaceutical composition comprising a compound of formula (1) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (1) or a pharmaceutically acceptable salt thereof as hereinbefore defined, with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The ability of compounds which can inhibit PMA/ionomycin-stimulated peripheral blood mononuclear cell proliferation can be assessed, for example using the procedure set out below:

The invention will now be illustrated in the following Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) yields are given for illustration only and are not necessarily the maximum attainable;

(iv) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; triplet; m, multiplet; br, broad; q, quartet, quin, quintet;

(v) intermediates were not generally fully characterised and purity was assessed by thin layer chromatography (TLC), high-performance liquid chromatography (HPLC), mass spectrometry (MS), infra-red (IR) or NMR analysis;

| Abbreviations | |
| --- | --- |
| Dimethylformamide | DMF |
| Tetrahydrofuran | THF |

The following examples illustrate the invention.

EXAMPLE 1

2-[(3,5-dimethyl]-1H-pyrazol-4-yl)methyl]-3-[[(4S)-4-hydroxy-2-isoxazolidinyl]carbonyl-5-methyl-7-(1-methylethyl)thieno[2,3,-d]pyridazin-4(5H)-one

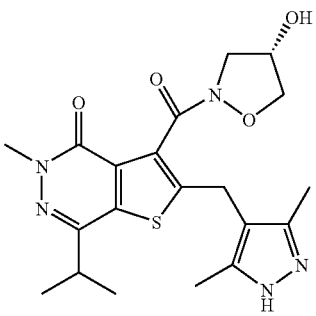

a) 2-(2-Methyl-1-oxopropyl)-3-thiophenecarboxylic acid

To a solution of thiophene-3-carboxylic acid (26.65 g) in THF (300 ml) was added 2M lithium diisopropylamide (229 ml) dropwise at 0–5° C. with stirring under nitrogen, and the resulting mixture stirred for 15 min. A solution of N-methoxy-N,2-dimethylpropanamide (30 g) in THF (150 ml) was added dropwise over a period of 1 hr. When the addition was complete, the reaction mixture was allowed to warm to room temperature and stirred for 2 hr. It was poured onto water, the layers separated and the aqueous washed with ether. The aqueous was acidified with conc. hydrochloric acid and extracted with ethyl acetate, the organic extracts were dried over anhydrous magnesium sulfate, filtered and evaporated under reduced pressure to give the sub-title compound as a solid (38.91 g).

$\delta^1H_{DMSO}$ 1.10 (6H, d), 3.30 (1H, m), 7.37 (1H, d), 7.85 (1H, d)

b) 5-Methyl-7-(1-methylethyl-thieno[2,3-d]pyridazin-4(5H)-one

Prepared from a solution of the product of part a) (38.91 g) and methylhydrazine (11.48 ml) in ethanol (200 ml) which was heated at reflux for 2 hr. and concentrated under reduced pressure. The residue was purified by column chromatography over silica, eluting with ethyl acetate/i-hexane (1:4) followed by ethyl acetate/i-hexane (1:1)to give the sub-title compound as a solid (33.09 g).

MS (ESI) 209 [M+H]$^+$ $\delta^1H_{CDCl_3}$ 1.39(6H, d), 3.13 (1H, septet), 3.85 (3H, s), 7.59 (1H, d), 7.75 (1H, d)

c) 2-Bromo-5-methyl-7-(1-methylethyl-thieno[2,3-d]pyridazin-4(5H)-one

Prepared from a solution of the product of part b) (33.09 g) in acetic acid (100 ml) and water (100 ml) which was treated with bromine (8.16 ml) dropwise over a period of 5 min with stirring under nitrogen The mixture was heated at 70° C. for 6 hr. then cooled, diluted with sodium sulfite solution and extracted with ethyl acetate. The organic extracts were dried over anhydrous magnesium sulfate, filtered and evaporated under reduced pressure. The residue was purified by column chromatography over silica, eluting with ethyl acetate/i-hexane (1:19) followed by ethyl acetate/i-hexane (1:4) to give the sub-title compound as a solid (13.0 g).

MS (ESI) 287 and 289 [M+H]$^+$ $\delta^1H_{CDCl_3}$ 1.35 (6H, d), 3.01 (1H, septet), 3.82 (3H, s), 7.71 (1H, s)

d) 1-(Diphenylmethyl)-3,5-dimethyl-(1H)-pyrazole-4-carboxaldehyde

To a hot solution of 1-(diphenylmethyl)-3,5-dimethyl-(1H)-pyrazole (25.0 g) in DMF (22 ml) was added phosphoryl chloride (8.87 ml) dropwise with stirring under nitrogen and the resulting mixture heated at 100° C. for 3 hr. It was cooled, diluted with water and dichloromethane and basified with 50% sodium hydroxide with ice/water cooling. It was extracted with dichloromethane, the organic extracts washed with water, dried over anhydrous magnesium sulfate, filtered and evaporated under reduced pressure. The residue was purified by column chromatography over silica, eluting with ethyl acetate/i-hexane (1:19) followed by ethyl acetate to give the sub-title compound as a solid (12.61 g).

$\delta^1H_{DMSO}$ 2.49 (3H, s), 3.58(3H, s), 6.91 (1H, s), 7.19–7.22 (4H, m), 7.29–7.38 (6H, m), 9.89 (1H, s)

e) 3-Bromo-2-[[1-(diphenylmethyl)-3,5-dimethyl-1H-pyrazol-4-yl]hydroxymethyl]-5-methyl-7-(1-methylethyl)-thieno[2,3-d]pyridazin-4(5H)-one To a solution of the product of part c) (13.0 g) in THF (100 ml) was added 2M lithium diisopropylamide (24.9 ml) dropwise at 0–5° C. with stirring under nitrogen, and the resulting mixture stirred for 20 min. A solution of the product of part d) (14.4 g) in THF (50 ml) was added dropwise, the mixture allowed to warm to room temperature and stirred for 3 hr. It was poured into sodium bicarbonate solution and extracted with ethyl acetate, the organic extracts washed with water, dried over anhydrous magnesium sulfate, filtered and evaporated under reduced pressure. The residue was purified by column chromatography over silica, eluting with ethyl acetate/1-hexane (1:4) followed by ethyl acetate/1-hexane (1:2) to give the subtitle compound as a solid (17.42 g).

MS (ESI) 577 and 579 [M+H]$^+$ $\delta^1H_{DMSO}$ 1.30 (6H, d), 2.00 (3H, s), 2.27 (3H, s), 3.13 (1H, septet), 3.65 (3H, s), 5.88 (1H, d), 6.51 (1H, d), 6.75 (1H, s), 7.10–7.12 (2H, m), 7.17–7.20 (2H, m), 7.25–7.35 (6H, m)

f) 3-Bromo-2-[1-(diphenylmethyl)-3,5-dimethyl-1H-pyrazol-4-ylmethyl]-5-methyl-7-(1-methylethyl)-thieno[2,3-d]pyridazin-4(5H)-one To a solution of the product of part e) (17.42 g) in dichloromethane (36 ml) and trifluoroacetic acid (72 ml) was added triethylsilane (36 ml) and the mixture heated at 40° C. with stirring under nitrogen for 48 hr. The solvent was removed under reduced pressure, the residue dissolved in ethyl acetate, washed successively with saturated sodium bicarbonate solution and water, dried over magnesium sulfate, filtered and evaporated under reduced pressure. The solid residue was triturated with i-hexane, collected by filtration and dried, to give the sub-title compound (16.19 g)

MS (ESI) 561 and 563 [M+H]$^+$ $\delta^1H_{DMSO}$ 1.23 (6H, d), 2.04 (3H, s), 2.20 (3H, s), 2.98 (1H, septet), 3.66 (3H, s), 3.97 (2H, s), 6.79 (1H, s), 7.16–7.18 (4H, m), 7.27–736 (6H, m)

g) 2-[1-(Diphenylmethyl)-3,5-dimethyl-1H-pyrazol-4-ylmethyl]-4,5-dihydro-5-methyl-7-(1-methylethyl)-4-oxo-thieno[2,3-d]pyridazine-3-carboxylic acid To a solution of the product of part f) (16.19 g) in anhydrous THF (200 ml) was added 2M isopropylmagnesium chloride solution (15.87 ml) dropwise at 0–5° C. with stirring under nitrogen, and the resulting mixture stirred at 0° C. for 30 min. It was then quenched with a stream of carbon dioxide for 2 hr, allowing the mixture to warm to room temperature. It was concentrated under reduced pressure and diluted with 1M hydrochloric acid. It was extracted with ethyl acetate, the organic extracts washed with water, dried over anhydrous magnesium sulfate, filtered and evaporated under reduced pressure to give the sub-title compound as a solid (15.18 g)

Ms (ESI) 527 [M+H]$^+$ $\delta^1H_{DMSO}$ 1.26 (6H, d), 2.03 (3H, s), 2.17 (3H, s), 3.07 (11H, septet), 3.82 (3H, s), 4.40 (2H, s), 6.82 (1H, s), 7.15–7.20 (4H, m), 7.28–7.3 8 (6H, m), 16.24 (1H, s, br)

h) 2-[3,5-Dimethyl-1H-pyrazol-4-ylmethyl]-4,5-dihydro-5-methyl-7-(1-methylethyl)-4-oxo-thieno[2,3-d]pyridazine-3-carboxylic acid To a solution of the product of part g) (15.18 g) in ethanol (100 ml) and formic acid (50 ml), under nitrogen, was added a catalytic amount of 10% palladium on alumina and the mixture stirred at ambient temperature for 18 h. The catalyst was removed by filtration, fresh catalyst added to the filtrate under nitrogen and the mixture stirred for 24 hr. It was filtered and the solvent removed under reduced pressure to give the sub-title compound as a solid (8.23 g)

MS (ESI) 361 [M+H]$^+$ $\delta^1H_{DMSO}$ 1.24 (6H, d), 2.08 (6H, s), 3.10 (1H, pent), 3.81 (3H, s), 4.36 (2H, s)

i) 2-[3,5-Dimethyl-1H-pyrazol-4-ylmethyl]-3-[[(4S)-4-hydroxy-2-isoxazolidinyl]carbonyl]-5-methyl-7-(1-methylethyl)thieno[2,3-d]pyridazin-4(5H)-one To a suspension of the product of part h) (7.13 g), (S)-4-isoxazolidinol hydrochloride (2.73 g), and 1-hydroxybenzotriazole (3.33 g) in acetonitrile (250 ml) was added triethylamine (12.12 ml) followed by diethyl chlorophosphate (3.16 ml) and the mixture stirred at ambient temperature under nitrogen for 18 hr. It was concentrated under reduced pressure, diluted with saturated sodium bicarbonate solution and extracted with ethyl acetate. The organic extracts were washed with water, dried over anhydrous magnesium sulfate, filtered and evaporated under reduced pressure. The residue was purified by column chromatography over silica, eluting with ethyl acetate/methanol (49:1) followed by ethyl acetate/methanol (19:1) to give the title compound as a solid (2.1 g).

MS (APCI) 432 [M+H]$^+$ $\delta^1H_{DMSO}$ 1.23–1.26 (6H, m), 2.07–2.11 (6H, m), 2.98–3.04 (1H, m), 3.48–4.16 (9H, m), 4.67–4.79 (1H, m), 5.51–5.55 (1H, m), 12.16 (1H, s, br)

EXAMPLE 2

2-[(3,5-Dimethyl-1H-pyrazol-4-yl)methyl]-3-[[(4S)-4-hydroxy-2-isoxazolidinyl]carbonyl]-5-methyl-7-(2-methylpropyl)thieno[2,3-d]pyridin-4(5H)-one

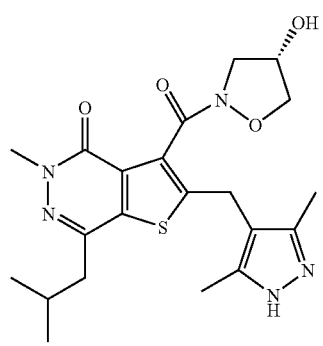

a) 2-Bromo-5-methyl-7-(2-methylpropyl)thieno[2,3-d]pyridazin-4(5H-one

Prepared from 5-methyl-7-(2-methylpropyl)thieno[2,3-d]pyridazin-4(5H)-one (WO 9929695) following the procedure of example 1, part c) to give the sub-title compound as a solid.

MS(ESI) 301 and 303 [M+H]$^+$ $\delta^1H_{CDCl3}$ 0.98 (6H, d), 2.19 (1H, septet), 2.59 (2H, d), 3.82 (3H, s), 7.69 (1H, s)

b) 3-Bromo-2-[[1-(diphenylmethyl)-3,5-dimethyl-1H-pyrazol-4-yl]hydroxymethyl]-5-methyl-7-(2-methylpropyl)thieno[2,3-d]pyridazin-4(5H)-one Prepared from the product of part a) following the procedure of example 1 part e) to give the sub-title compound as a solid.

$\delta^1H_{DMSO}$ 0.94–0.96 (6H, m), 1.99 (3H, s), 2.11 (1H, septet), 2.26 (3H, s), 2.61–2.68 (2H m), 3.66 (3H, s), 5.88 (1H, d), 6.53 (1H, d), 6.91 (1H, s), 7.10–7.20 (4H, m), 7.25–7.38 (6H, m)

c) 3-Bromo-2-[[1-(diphenylmethyl)-3,5-dimethyl-1H-pyrazol-4-yl]methyl-5-methyl-7(2-methylpropyl)thieno[2,3-d]pyridazin-4(5H)-one Prepared from the product of part b) following the procedure of example 1 part f) to give the sub-title compound as a solid.

MS(ESI) 575 and 577 [M+H]+

$\delta^1H_{DMSO}$ 0.88 (6H, d), 1.99 (3H, s), 1.99–2.04 (1H, m), 2.15 (3H, s), 3.66 (3H, s), 3.97 (2H, s), 6.80 (1H, s), 7.15–7.37 (6H, m)

d) 2-[[1-(Diphenylmethyl)-3,5-dimethyl-1H-pyrazol-4-yl]methyl]-4,5-dihydro-5-methyl-7-(2-methylpropyl)-4-oxo-thieno[2,3-d]pyridazine-3-carboxylic acid Prepared from the product of part c) following the procedure of example 1 part g) to give the sub-title compound as a solid.

MS(ESI) 541 [M+H]$^+$ e) 2-[(3,5-Dimethyl-1H-pyrazol-4-yl)methyl-4,5-dihydro-5-methyl-7-(2-methylpropyl)-4-oxo-thieno[2,3-d]pyridazine-3-carboxylic acid Prepared from the product of part d) following the procedure of example 1 part h) to give the subtitle compound as a solid

MS(ESI) 375 [M+H]$^+$ $\delta$ $^1$H$_{DMSO}$ 0.89 (6H, d), 2.07–2.13 (7H, m), 2.62 (2H, d), 3.81 (3H, s), 4.34 (2H, s)

f) 2-[(3,5-Dimethyl-1H-pyrazol-4-yl)methyl]3-[[(4S)-4-hydroxy-2-isoxazolidinyl]carbonyl]-5-methyl-7-(2-methylpropyl)thieno[2,3-d]pyridazin-4(5H)-one Prepared from the product of part e) following the procedure of example 1 part i) to give the title compound as a solid.

MS(APCI) 446 [M+H]$^+$ $\delta$ $^1$H$_{DMSO}$ 0.89–0.91 (6H, m), 2.04–2.12 (7H, m), 2.55–2.58 (2H, m), 3.48–4.16 (9H, m), 4.63–4.80 (1H, m), 5.52 (1H, S, br)

EXAMPLE 3

2-[(3,5-dimethyl-1H-pyrazol-4-yl)methyl]-7-ethyl-3-[[(4S)-4-hydroxy-2-isoxazolidinyl]carbonyl]-5-methyl-thieno[2,3-d]pyridazin-4(5H)-one

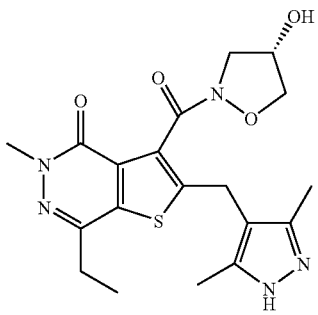

a) N-methoxy-N-methylpropanamide

To a solution of propanoyl chloride (15 ml) in DCM (250 ml) under nitrogen was added N,O-dimethylhydroxylamine (17 g) and triethylamine (72 ml) at 0° C. with stirring. The resulting mixture was allowed to warm to room temperature over 5 h then filtered, the filtrate evaporated under reduced pressure and then triturated with diethyl ether. The resulting filtrate was evaporated under reduced pressure to give the sub-title compound as an oil (17.7 g)

$\delta$ $^1$H$_{CDCl3}$ 1.14 (3H, t), 2.43 (2H, q), 3.08 (3H, s), 3.67 (3H, a)

b) 2-(1-Oxopropyl)-3-thiophenecarboxylic acid

Prepared from thiophene-3-carboxylic acid and the product of part a) following the procedure of example 1, part a) to give the sub-title compound as a solid.

$\delta$ $^1$H$_{CDCl3}$ 1.91 (3H, t), 3.18 (2H, q), 7.64 (1H, d), 7.98 (1H, d)

c) 5-Methyl-7-ethyl-thieno[2,3-d]pyridazin-4(5H)-one

Prepared from the product of part b) following the procedure of example 1, part b) to give the sub-title compound as a solid.

$\delta$ $^1$H$_{CDCl3}$ 1.38 (3H, t), 2.86 (2H, q), 3.85 (3H, s), 7.60 (1H, d), 7.75 (1H, d)

d) 2-Bromo-7-ethyl-5-methyl-thieno[2,3-d]pyridazin-4(5H)-one

Prepared from a solution of the product of part c) (4.8 g) in DCM (50 ml) which was treated with methanesulfonic acid (0.8 ml) and 1,3-dibromo-5,5-dimethylhydantoin (3.5 g). The mixture was stirred under nitrogen, in the dark, for 20 h. Additional methanesulfonic acid (0.8 ml) and 1,3-dibromo-5,5-dimethylhydantoin (3.5 g) were added and the mixture stirred for a further 20 h. The mixture was diluted with DCM and successively washed with sodium thiosulfate solution (×2) then brine, dried over anhydrous magnesium sulfate, filtered and evaporated under reduced pressure. The residue was purified by column chromatography over silica, eluting with isohexane/ethyl acetate (9:1) followed by isohexane/ethyl acetate (8:2) to give the sub-title compound as a solid (3 g).

$\delta$ $^1$H$_{CDCl3}$ 1.35 (3H, t), 2.77 (2H, q), 3.82 (3H s), 7.70 (1H, s)

e) 3-Bromo-2-[[1-(diphenylmethyl)-3,5-dimethyl-1H-pyrazol-4-yl]hydroxymethyl]-7-ethyl-5-methyl-thieno[2,3-d]pyridazin-4(5H)-one Prepared from the product of part d) following the procedure of example 1, part e) to give the sub-title compound as a solid.

MS (ESI) 563 and 565 [M+H]$^+$ $\delta$H$_{CDCl3}$ 1.35 (3H, t), 2.15 (3H, s), 2.23 (3H, s), 2.81 (2H, q), 3.80 (3H, s), 6.04 (1H, s), 6.56 (1H, s), 7.08–7.17 (4H, m), 7.26–7.35 (6H, m)

f) 3-Bromo-2-[[1-(diphenylmethyl)-3,5-dimethyl-1H-pyrazol-4-yl]methyl]-7-ethyl-5-methyl-thieno[2,3-d]pyridazin-4(5H)-one Prepared from the product of part e) following the procedure of example 1, part f) to give the sub-title compound as a solid.

MS (ESI) 547 and 549 [M+H]$^+$ $\delta$ $^1$H$_{CDCl3}$ 1.28 (3H, t), 2.10 (3H, s), 2.18 (3H, s), 2.74 (2H, q), 3.80 (3H, s), 3.93 (2H, s), 6.91 (1H, s), 7.15 (4H, m), 7.33 (6H, m)

g) 2-[[1-(Diphenylmethyl)-3,5-dimethyl-1H-pyrazol-4-yl]methyl]-7-ethyl-4,5-dihydro-5-methyl-4-oxo-thieno[2,3-d]pyridazine-3-carboxylic acid Prepared from the product part f) following the procedure of example 1, part g) to give the sub-title compound as a solid.

MS (ESI) 513 M+H]$^+$ $\delta$ $^1$H$_{CDCl3}$ 1.34 (3H, t), 2.07 (3H, s), 2.15 (3H, s), 2.79 (2H, q), 3.93 (3H, s), 4.55 (2H, s), 6.64 (1H, s), 7.17 (4H, m), 7.32 (6H, m)

h) 2-[(3,5-Dimethyl-1H-pyrazol-4-yl)methyl]-7-ethyl-4,5-dihydro-5-methyl-4-oxo-thieno[2,3-d]pyridazine-3-carboxylic acid Prepared from the product of part g) following the procedure of example 1, part h) to give the sub-title compound as a solid.

MS (ESI) 347 [M+H]$^+$ $\delta^1H_{DMSO}$ 1.22 (3H, t), 2.08 (6H, s), 2.79 (2H, q), 3.81 (3H, s), 4.32 (2H, s)

i) 2-[(3,5-Dimethyl-1H-pyrazol-4-yl)methyl]-7-ethyl-3-[[(4S)-4-hydroxy-2-isoxazolidinyl]carbonyl]-5-methyl-thieno[2,3-d]pyridazin-4(5H)-one Prepared from the product of part h) following the procedure of example 1, part i) to give the sub-title compound as a solid.

MS (ESI) 418 [M+H]$^+$ $\delta^1H_{DMSO}$ 1.23 (3H, m), 2.05 (3H, m), 2.13 (3H, m), 2.74 (2H, m), 3.33 (3H, s), 3.51–4.16 (6H, m), 4.61–4.82 (1H, m), 5.55 (1H, m).

EXAMPLE 4

7-Cyclopropyl-2-[3,5-dimethyl-1H-pyrazol-4-yl)methyl]-3-[[(4S)-4-hydroxy-2-isoxazolidinyl]carbonyl]-5-methyl-thieno[2,3-d]pyridazin-4(5H)-one

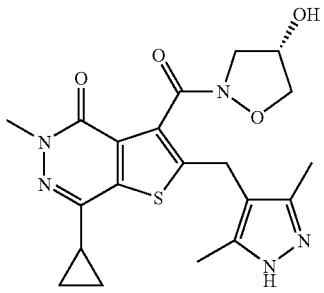

a) N-methoxy-N-methyl-cyclopropanecarboxamide

Prepared from cyclopropanecarbonyl chloride following the procedure of example 3, part a) to give the sub-title compound as an oil.

$\delta^1H_{CDCl3}$ 0.81 (2H, m), 0.99 (2H, m), 2.14 (1H, m), 321 (3H, s), 3.67 (3H, s)

b) 2-(Cyclopropylcarbonyl-3-thiophenecarboxylic acid

Prepared from thiophene-3-carboxylic acid and the product of part a) following the procedure of example 1, part a) to give the sub-title compound as a solid.

$\delta^1H_{CDCl3}$ 1.31 (2H, m), 1.48 (2H, m), 2.59 (1H, m), 7.70 (1H, d), 7.98 (1H, d)

c) 7-Cyclopropyl-5-methyl-thieno[2,3-d]pyridazin-4(5H)-one

Prepared from the product of part b) following the procedure of example 1, part b) to give the sub-title compound as a solid.

MS (ESI) 207 [M+H]$^+$ $\delta^1H_{CDCl3}$ 1.02 (2H, m), 1.08 (2H, m), 2.02 (1H, m), 3.78 (3H, s), 7.59 (1H, d), 7.75 (1H, d)

d) 2-Bromo-7-cyclopropyl-5-methyl-thieno[2,3-d]pyridazin-4(5H)-one

Prepared from a rapidly stirred solution of the product of part c) (9.0 g) in saturated sodium bicarbonate solution (150 ml), treated with bromine 6.7 ml. After 25 min. sodium metabisulfite solution was added dropwise and with stirring and sonicating a solid was formed. The resulting solid was filtered, washed with water, dried in a vacuum oven and purified by column chromatography over silica, eluting with iso-hexane/ethyl acetate (9:1) to give the sub-title compound as a solid (8.0 g).

$\delta^1H_{CDCl3}$ 1.04 (4H, m), 1.84 (1H, m), 3.77 (3H, s), 7.69 (1H, s)

e) 3-Bromo-7-cyclopropyl-2-[[1-(diphenylmethyl)-3,5-dimethyl-1H-pyrazol-4-yl]hydroxymethyl]-5-methyl-thieno[2,3-d]pyridazin-4(5H)-one Prepared from the product of part d) following the procedure of example 1, part e) to give the sub-title compound as a solid.

MS (ESI) 575 and 577 [M+H]$^+$ $\delta^1H_{CDCl3}$ 1.05 (4H, m), 1.92 (1H, m), 2.17 (3H, s), 2.24 (3H, s), 3.75 (3H, s), 6.06 (1H, s), 6.57 (1H, s), 7.15 (4H, m), 7.32 (6H, m)

f) 3-Bromo-7-cyclopropyl-2-[[1-(diphenylmethyl)-3,5-dimethyl-1H-pyrazol-4-yl]methyl]-5-methyl-thieno[2,3-d]pyridazin-4(5H)-one Prepared from the product of part e) following the procedure of example 1, part f) to give the sub-title compound as a solid.

MS (ESI) 559 and 561 [M+H]$^+$ $\delta^1H_{CDCl3}$ 0.98 (4H, m), 1.83 (1H, m), 2.13 (3H, s), 2.19 (3H, s), 3.75 (3H, s), 3.94 (3H, s), 6.61 (1H, s), 7.16 (4H, m), 7.31 (6H, m)

g) 7-Cyclopropyl-2-[[1-(diphenylmethyl)-3,5-dimethyl-1H-pyrazol-4-yl]methyl]-4,5-dihydro-5-methyl-4-oxo-thieno[2,3-d]pyridazine-3-carboxylic acid Prepared from the product of part f) following the procedure of example 1, part g) to give the sub-title compound as a solid.

MS (ESI) 525 [M+H]$^+$ $\delta^1H_{CDCl3}$ 1.06 (4H, m), 1.87 (1H, m), 2.05 (3H, s), 2.19 (3H, s), 3.84 (3H, s), 4.56 (2H, s), 6.63 (1H, s), 7.18 (4H, m), 7.35 (6H, m)

h) 7-Cyclopropyl-2-[(3,5-dimethyl-1H-pyrazol-4-yl)methyl]-4,5-dihydro-5-methyl-4-oxo-thieno[2,3-d]pyridazine-3-carboxylic acid Prepared from the product of part g) following the procedure of example 1, part h) to give the sub-title compound as a solid.

MS (ESI) 359 [M+H]$^+$ $\delta^1H_{DMSO}$ 0.95 (4H, m), 2.18 (6H, s), 2.20 (1H, m), 3.77 (3H, s), 4.39 (2H, s)

i) 7-Cyclopropyl-2-[(3,5-dimethyl-1H-pyrazol-4-yl)methyl]-3-[[(4S)-4-hydroxy-2-isoxazolidinyl]carbonyl]-5-methyl-thieno[2,3-d]pyridazin-4(5H)-one Prepared from a solution of part h) following the procedure of example 1, part i) to give the title compound as a solid.

MS (ESI) 430 [M+H]$^+$ $\delta\,^1H_{DMSO}$ 0.92 (4H, m), 2.03 (3H, m), 2.14 (31, m), 3.32 (3H, s), 3.50–4.14 (6H, m), 4.56–4.79 (11H, m), 5.54 (1H, m)

EXAMPLE 5

7-Cyclopropyl-2-[(3,5-dimethyl-1H-pyrazol-4-yl)methyl]-5-ethyl-3-[[(4S)-4-hydroxy-2-isoxazolidinyl]carbonyl]-thieno[[2,3-d]pyridazin-4(5H)-one

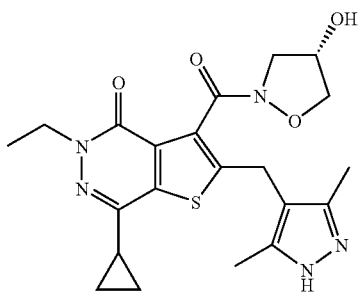

a) 7-Cyclopropyl-5-ethyl-thieno[2,3-d]pyridazin-4(5H)-one

Prepared from a suspension of the product of example 4, part b) (12.0 g) in ethanol (150) which was treated with triethylamine (19 ml) and ethylhydrazine oxalate (9.9 g). The mixture was refluxed for 6 hr, then allowed to cool and evaporated under reduced pressure. The resulting oil was partitioned between 1N sodium hydroxide solution and dichloromethane. The organic layer was separated, washed with 1N sodium hydroxide solution, brine and then water, dried over anhydrous magnesium sulfate, filtered and evaporated under reduced pressure to give the sub-title compound as an oil (10.8 g).

MS (ESI) 221 [M+H]$^+$ $\delta\,^1H_{CDCl3}$ 1.02 (2H, m), 1.11 (2H, m), 1.38 (3H, t), 2.02 (1H, m), 4.24 (2H, q), 7.58 (1H, d), 7.75(1H, d)

b) 2-Bromo-7-cyclopropyl-5-ethyl-thieno[2,3-pyridazin-4(5H)-one

Prepared from the product of part a) following the procedure of example 4, part d) to give the sub-title compound as a solid.

MS (ESI) 299 and 301 [M+H]$^+$ $\delta\,^1H_{CDCl3}$ 1.04 (4H, m), 1.37 (3H, t), 1.84 (1H, m), 4.20 (2H, q), 7.70 (1H, s)

c) 3-Bromo-7-cyclopropyl-2-[[1-(diphenylmethyl)-3,5-dimethyl-1H-pyrazol-4-yl]hydroxymethyl]-5-ethyl-thieno[2,3-d]pyridazin-4(5H)-one Prepared from the product of part b) following the procedure of example 1, part e) to give the sub-title compound as a solid.

MS (ESI) 895 and 591 [M+H]$^+$ $\delta\,^1H_{CDCl3}$ 1.01 (2H, m), 1.05 (2H, m), 1.37 (3H, t), 1.92 (1H, m), 2.18 (3H, s), 2.24 (3H, s), 4.19 (2H, m), 6.06 (1H, s), 6.57 (1H, s), 7.09 (2H, m), 7.12 (2H, m), 7.31 (6H, m)

d) 3-Bromo-7-cyclopropyl-2-[[1-(diphenylmethyl)-3,5-dimethyl-1H-pyrazol-4-yl]methyl]-5-ethyl-thieno[2,3-d]pyridazin-4(5H)-one Prepared from the product of part c) following the procedure of example 1, part f) to give the sub-title compound as a solid.

MS (ESI) 573 and 575 [M+H]$^+$ $\delta\,^1H_{CDCl3}$ 0.97–1.05 (4H, m), 1.35 (3H, t), 1.82 (11H, m), 2.12 (3H, s), 2.17 (3H, s), 3.94 (2H, s), 4.19 (2H, q), 6.61 (1H, s), 7.16 (4H, m), 7.35 (6H, m)

e) 7-Cyclopropyl-2-[[1-(diphenylmethyl)-3,5-dimethyl-1H-pyrazol-4-yl]methyl-5-ethyl-4,5-dihydro-4-oxo-thieno[2,3-d]pyridazine-3-carboxylic acid Prepared from the product of part d) following the procedure of example 1, part g) to give the sub-title compound as a solid.

MS (ESI) 539 [M+H]$^+$ $\delta\,^1H_{CDCl3}$ 1.04 (4H, m), 1.39 (3H, t), 1.88 (1H, m), 2.06 (3H, s), 2.15 (3H, s), 4.28 (2H, q), 4.56 (2H, s), 6.65 (1H, s), 7.17 (4H, m), 7.34 (6H, m)

f) 7-Cyclopropyl-2-[(3,5-dimethyl-1H-pyrazol-4-yl)methyl]-5-ethyl-4,5-dihydro-4-oxo-thieno[2,3-d]pyridazine-3-carboxylic acid Prepared from the product of part e) following the procedure of example 1, part h) to give the sub-title compound as a solid.

MS (ESI) 373 [M+H]$^+$ g) 7-Cyclopropyl-2-[(3,5-dimethyl-1H-pyrazol-4-yl)methyl]-5-ethyl-3-[[(4S)-4-hydroxy-2-isoxazolidinyl]carbonyl]-thieno[2,3-d]pyridazin-4(5H)-one Prepared from a solution of the product of part f) (260 mg) in dichloromethane (4 ml) which was treated with (S)-4-isoxazolidinol hydrochloride (105 mg), PyBrOP (285 mg) and triethylamine (0.23 ml) and stirred at room temperature for 3 days. The reaction mixture was directly purified by column chromatography over silica, eluting with dichloromethane/methanol 98:2 followed by dichloromethane/methanol 96:4 then preparative reverse phase HPLC using acetonitrile/aq. ammonia to give the title compound as a solid (80 mg).

MS (ESI) 444M+H]$^+$ $\delta\,^1H_{DMSO}$ 0.93 (4H, m), 1.37–1.43 (3H, m), 1.97–2.16 (7H, m), 3.58–3.94 (9H, m), 5.39–5.60 (1H, m), 12.17 (1H, bs)

EXAMPLE 6

2-[(3,5-Dimethyl-1H-pyrazol-4-yl)methyl]-3-[[(4S)-4-hydroxy-4-methyl-2-isoxazolidinyl]carbonyl-5-methyl-7-(1-methylethyl)thieno[2,3-d]pyridazin-4(5H)-one

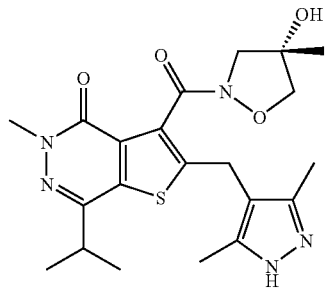

a) 2-[[(2S)-2-Methyloxiranyl]methoxy]-1H-isoindole-1,3(2H)-dione

A mixture of N-hydroxypthalimide (5.3 g), [(2S)-2-methyloxiran-2-yl]methyl 3-nitrobenzenesulfonate (5.9 g) and triethylamine (10.6 ml) in dichloromethane (15 ml) was stirred under nitrogen at ambient temperature for 24 hours. The reaction mixture was poured onto a silica column and eluted with dichloromethane to give the sub-title compound as a colourless solid (3.1 g).

MS (APCI) 234 [M+H]$^+$ $\delta\,^1H_{CDCl_3}$ 1.63 (3H, s), 2.69 (1H, d), 2.76 (1H, d), 4.17 (1H, d), 4.21 (1H, d), 7.73–7.78 (2H, m), 7.82–7.87 (2H, m)

b) 2-[[(2R)-3-Chloro-2-hydroxy-2-methylpropyl]oxy]-1H-isoindole-1,3(2H)-dione The product of part a) (3.0 g) was treated with concentrated hydrochloric acid (12 ml) and stirred at ambient temperature for 2 hours. The mixture was partitioned between water and dichloromethane, the organics were dried and purified by chromatography (EtOAc) to give the sub-title compound as a colourless solid (3.3 g).

$\delta\,^1H_{DMSO}$ 1.29(3H, S), 3.67 (1H, d), 3.76 (1H, d), 4.09 (1H, d), 4.15 (1H, d), 7.86 (4H, s), 5.24 (1H, s)

c) 2-[[(4S)-4-Hydroxy-4-methyl-2-isoxazolidinyl]carbonyl]-benzoic acid methyl ester Prepared from a solution of the product of part b) (3.3. g) in methanol (25 ml) which was treated with triethylamine (3.4 ml) and heated under nitrogen at reflux for 1 hour. The mixture was concentrated to dryness and purified by chromatography over silica eluting with a gradient from dichloromethane to 5% methanol in dichloromethane. The chiral purity of the product was enhanced by recrystallising twice from acetonitrile to give the subtitle compound as a colourless solid (1.92 g).

HPLC: (9010THIP.M) 50 mm chiracel AD column, ee>99%

$\delta\,^1H_{CDCl_3}$ 1.52 (3H, s), 3.59 (1H, d), 3.81 (1H, d), 3.88 (1H, d), 4.04 (1H, s), 4.34 (1H, d), 3.92 (3H, s), 7.45 (1H, d), 7.49 (1H, t), 7.62 (1H, t), 8.00 (1H, d).

d) (4S)-4-Methyl-4-isoxazolidinol hydrochloride

Prepared from a solution of the product of part c) (4.9 g) in 2N hydrochloric acid (30 ml) which was heated under nitrogen at reflux for 4 hours. After cooling the precipitate was removed by filtration and the liquors concentrated to dryness under vacuo. The residue was triturated with acetonitrile to give the sub-title compound as a white solid (1.79 g).

$\delta\,^1H_{DMSO}$ 1.42 (3H, s), 3.29 (1H, d), 3.41 (1H, dd), 3.87 (1H, d), 4.05 (1H, dd).

e) 2-[(3,5-Dimethyl-1H-pyrazol-4-yl)methyl]-3-[[(4S)-4-hydroxy-4-methyl-2-isoxazolidinyl]carbonyl-5-methyl-7-(1-methylethyl)thieno[2,3-d]pyridazin-4(5H)-one To a solution of the product of part d) (85 mg), the product of example 1 part h) (201 mg) and PyBroP (285 mg) in DCM (5 ml) was added triethylamine (0.23 ml) and the mixture stirred at room temperature under nitrogen for 18 hr. It was concentrated in vacuo and the residue was purified by column chromatography over silica, eluting with ethyl acetate/methanol (50:1) to give the title compound as a solid (129 mg).

MS (APCI) 446 [M+H]$^+$ $\delta\,^1H_{DMSO}$ 1.18–1.44 (9H, m), 2.08 (6H, d), 2.98–3.10 (2H, m), 3.57–4.00 (8H, m), 5.40 (0.66H, s), 5.76 (0.33H, s), 12.15 (1H, S, br)

EXAMPLE 7

2-[(3,5-Dimethyl-1H-pyrazol-4-yl)methyl]-3-[[(4S)-4-hydroxy-4-methyl-2-isoxazolidinyl]carbonyl]-5-methyl-7-(2-methylpropyl)-thieno[2,3-d]pyridazin-4(5H)-one

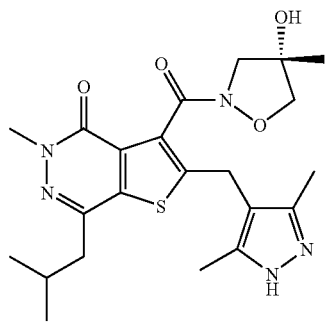

a) 2-[(3,5-Dimethyl-1H-pyrazol-4-yl)methyl]-3-[[(4S)-4-hydroxy-4-methyl-2-isoxazolidinyl]carbonyl]-5-methyl-7-(2-methylpropyl)-thieno[2,3-d]pyridazin-4(5H)-one Prepared from the product of example 2 part e) following the procedure of example 6 part e) to give the title compound as a solid.

MS(APCI) 460 [M+H]$^+$ $\delta\,^1H_{DMSO}$ 0.90 (6H, d), 1.27–1.44 (3H, m), 2.04–2.12 (7H, m), 2.55–2.59 (2H, m), 3.57–3.93 (9H, m), 5.40 (0.66H, s), 5.59 (0.33H, s), 12.16 (1H, s)

EXAMPLE 8

2-[(3,5-Dimethyl-1H-pyrazol-4-yl)methyl]-7-ethyl-3-[[(4S)-4-hydroxy-4-methyl-2-isoxazolidinyl]carbonyl]-5-methyl-thieno[2,3-d]pyridazin-4(5H)-one

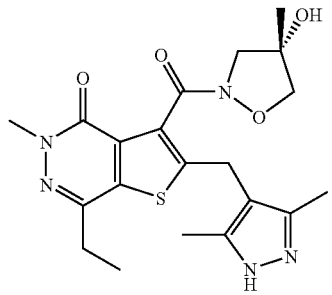

a) 2-[(3,5-Dimethyl-1H-pyrazol-4-yl)methyl]-7-ethyl-4,5-dihydro-5-methyl-4-oxo-thieno[2,3-d]pyridazine-3-carboxylic acid Prepared from the product of example 3, part g) (1.0 g) in trifluoroacetic acid (10 ml) under reflux for 20 hrs. The resulting mixture was evaporated under reduced pressure, azeotroping with dichloromethane (×3). The residue was triturated with water and then with ether, and the solid was collected and dried to give the subtitle compound as a solid (580 mg).

MS (ESI) 347 [M+H]$^+$ $\delta\,^1H_{DMSO}$ 1.22 (3H, t), 2.01 (6H, s), 2.80 (2H, q), 3.83 (3H, s), 4.39 (2H, s)

b) 2-[(3,5-Dimethyl-1H-pyrazol-4-yl)methyl]-7-ethyl-3-[[(4S)-4-hydroxy-4-methyl-2-isoxazolidinyl]carbonyl]-5-methyl-thieno[2,3-d]pyridazin-4(5H)-one Prepared from the product of part a) following the procedure of example 6, part e) to give the title compound as a solid.

MS (ESI) 432 [M+H]$^+$ $\delta\,^1H_{DMSO}$ 1.21 (3H, m), 1.25–1.44 (3H, m), 2.07 (6H, bs), 2.75 (2H, m), 3.63–3.94 (9H, m), 5.39–5.60 (1H, m), 12.16 (1H, bs)

EXAMPLE 9

7-Cyclopropyl-2-[3,5-dimethyl-1H-pyrazol-4-yl)methyl]-3-[[(4S)-4-hydroxy-4-methyl-2-isoxazolidinyl]carbonyl]-5-methyl-thieno[2,3-d]pyridazin-4(5H)-one

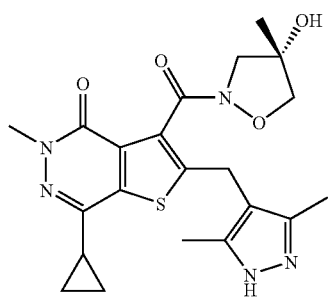

a) 7-Cyclopropyl-2-[(3,5-dimethyl-1H-pyrazol-4-yl)methyl]-3-[[(4S)-4-hydroxy-4-methyl-2-isoxazolidinyl]carbonyl]-5-methyl-thieno[2,3-d]pyridazin-4(5H)-one Prepared from the product of example 4, part h) following the procedure of example 6, part e) to give the title compound as a solid.

MS (ESI) 444 [M+H]$^+$ $\delta\,^1H_{DMSO}$ 0.93 (4H, m), 1.37–1.43 (3H, m), 1.97–2.16 (7H, m), 3.58–3.94 (9H, m), 5.39–5.60 (1H, m), 12.17 (1H, m)

EXAMPLE 10

3-[[(4S)-4-hydroxyisoxazolidinyl]carbonyl-5-methyl-7-(2-methylpropyl)-2-(1H-pyrrolo[2,3-b]pyridin-3-ylmethyl)thieno[2,3-d]pyridin-4(5H)-one

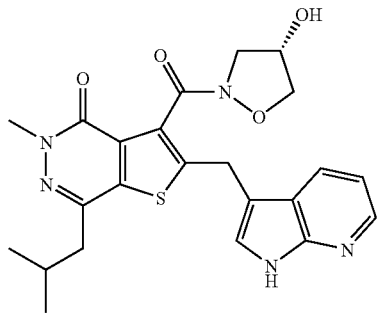

a) 3-Bromo-2-[hydroxy[1-(phenylsulphonyl)-1H-pyrrolo[2,3-b]pyrimidin-3-yl]methyl]-5-methyl-7-(2-methylpropyl)-thieno[2,3-d]pyridazin-4(5H)-one To a solution of the product of example 2 part a) (0.22 g) in anhydrous THF (5 ml) was added 2.0M LDA (0.44 ml) at −78° C. under nitrogen with stirring. After 20 mins a solution of 1-(phenylsulphonyl)1H-pyrrolo[2,3-b]pyridine-3-carboxaldehyde (0.23 g) in anhydrous THF (5 ml) was added and the mixture stirred at room temperature for 18 hr. It was poured into water and extracted with ethyl acetate. The organic extracts were washed with water, dried over anhydrous magnesium sulfate, filtered and evaporated under reduced pressure. The residue was purified by column chromatography over silica, eluting with i-hexane/ethyl acetate (1:1) to give the sub-title compound (0.2 g).

MS (ESI) 587 and 589 [M+H]$^+$ b) 3-Bromo-5-methyl-7-(2-methylpropyl)-2-[[1-(phenylsulphonyl)-1H-pyrrolo[2,3-b]pyrimidin-3-yl]methyl]-thieno[2,3-d]pyridazin-4(5H)-one To a solution of the product of part a) (0.2 g) in DCM (0.5 ml) was added triethylsilane (0.5 ml) and trifluoroacetic acid (1.0 ml) and the mixture stirred at 40° C. for 24 hr. It was concentrated in vacuo, diluted with sodium hydrogen carbonate solution and extracted with DCM. The organic extracts were washed with water, dried over anhydrous magnesium sulfate, filtered and evaporated under reduced pressure. The residue was purified by column chromatography over silica, eluting with i-hexane/ethyl acetate (3:1) to give the subtitle compound (0.17 g).

MS (ESI) 571 and 573 [M+H]$^+$ $\delta\,^1H_{CDCl_3}$ 0.94 (6H, d), 2.12 (1H, septet), 2.52 (2H, d), 3.82 (3H, s), 4.30 (2H, s), 7.14S 7.19 (1H, m), 7.47–7.61 (3H, m), 7.66 (1H, s), 7.76 (1H, dd), 8.20 (2H, d), 8.45 (1H, dd)

c) 4,5-Dihydro-5-methyl-7-(2-methylpropyl)-4-oxo-2-[[1-(phenylsulphonyl)-1H-pyrrolo[2,3-b]pyridin-3-yl]methyl]thieno[2,3-d]pyridazine-3-carboxylic acid To a solution of the product of part b) (0.17 g) in anhydrous THF (8 ml) was added 2.0M isopropylmagnesium chloride (0.164 ml) at o° C. and the mixture stirred for 5 mins. It was quenched with a stream of carbon dioxide for 45 mins. It was poured into water, acidified with dilute hydrochloric acid, and extracted with DCM. The organic extracts were washed with water, dried over anhydrous magnesium sulfate, filtered and evaporated under reduced pressure to give the sub-title compound as a solid (0.16 g).

MS (ESI) 537 [M+H]$^+$ d) 4,5-dihydro-5-methyl-7-(2-methylpropyl)-4-oxo-2-(1H-pyrrolo[2,3-b]pyridin-3-ylmethyl)thieno[2,3-d]pyridazine-3-carboxylic acid A solution of the product of part c) (0.16 g) in methanol (5 ml) was treated with potassium hydroxide (50 mg) and heated under reflux for 1.5 hr. It was concentrated in vacuo, acidified with dilute hydrochloric acid and extracted with DCM. The organic extracts were washed with water, dried over anhydrous magnesium sulfate, filtered and evaporated under reduced pressure to give the sub-title compound as a solid (0.10 g).

MS (ESI) 397 [M+H]$^+$ e) 3-[[(4S)-4-Hydroxyisoxazolidin-2-yl]carbonyl]-5-methyl-7-(2-methylpropyl)-2-(1H-pyrrolo[2,3-b]pyridin-3-ylmethyl)-thieno[2,3-d]pyridazin-4(5H)-one To a stirred suspension of the product of part d) (50 mg) in DCM (2 ml) under nitrogen was added 1-hydroxybenzotriazole hydrate (39 mg) and after 15 mins EDCI (48 mg) added and the mixture stirred for 1 hour. (S)-4-Isoxazolidinol hydrochloride (32 mg) and triethylamine (531 µl) were added and the mixture stirred overnight. It was diluted with water and extracted with DCM. The organic extracts were washed with water, dried over anhydrous magnesium sulfate, filtered and evaporated under reduced pressure. The residue was purified by column chromatography over silica, eluting with ethyl acetate/methanol (50:1) to give the title compound as a solid (19 mg).

MS(APCI) 468 [M+H]+

$\delta\,^1H_{DMSO}$ 0.85–0.87 (6H, m), 1.99–2.05 (1H, septet), 2.50 (2H, m), 3.55–3.62 (1H, m), 3.66 (31H, d), 3.73–3.78 (1H, m), 3.95–3.98 (1H, m), 4.14–4.19 (1H, m), 4.30–4.39 (2H, m), 4.67 (0.4H, m), 4.81 (0.61, m), 5.55 (1H, s, br), 7.00–7.03 (1H, m), 7.45–7.49 (1H, m), 7.89–7.94 (1H, m), 8.20–8.21 (1H, m), 11.59 (1H, s)

EXAMPLE 11

3-[[(4S)-4-Hydroxy-2-isoxazolidinyl]carbonyl]-5-methyl-7-(2-methylpropyl)-2-[[1,3,5-trimethylpyrazol-4-yl)methyl]-thieno[2,3-d]pyridazin-4(5H)-one

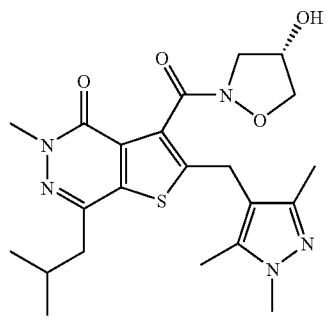

a) 3-Bromo-2-[hydroxy(1,3,5-trimethyl-1H-pyrazol-4-yl)methyl]-5-methyl-7-(2-methylpropyl)-thieno[2,3-d]pyridazin-4(5H)-one Prepared from the product of example 2 part a) and 1,3,5-pyrazole-4-carboxaldehyde by the method of example 10 part a) to give the sub-title compound.

MS (ESI) 439 and 441 [M+H]$^+$ $\delta\,^1H_{DMSO}$ 0.93—0.96 (6H, m), 2.01 (3H, s), 2.13 (1H, septet), 2.17 (3H, s), 2.59–2.69 (2H, m), 3.61 (3H, s), 3.66 (3H, s), 5.84 (1H, d), 6.43 (1H, d)

b) 3-Bromo-5-methyl-7-(2-methylpropyl)-2-[(1,3,5-trimethyl-1H-pyrazol-4-yl)methyl]-thieno[2,3-d]pyridazin-4(5H)-one Prepared from the product of part a) by the method of example 10 part b) to give the sub-title compound.

MS (ESI) 423 and 425 [M+H]$^+$ $\delta\,^1H_{DMSO}$ 0.88 (6H, d), 2.01 (3H, s), 2.05 (1H, septet), 2.17 (3H, s), 2.50–2.54 (2H, m), 3.66 (3H, s), 3.67 (3H, s), 3.93 (3H, s)

c) 4,5-Dihydro-5-methyl-7-(2-methylpropyl)-4-oxo-2-[(1,3,5-trimethyl-1H-pyrazol-4-yl)methyl]-thieno[2,3-d]pyridazine-3-carboxylic acid Prepared from the product of part b) by the method of example 10 part c) to give the sub-title compound as a solid.

MS (ESI) 389 [M+H]$^+$ $\delta\,^1H_{DMSO}$ 0.88 (6H, d), 2.00 (3H, s), 2.06 (1H, septet), 2.14 (3H, s), 2.56 (2H, d), 3.68 (3H, s), 3.82 (3H, s), 4.36 (2H, s), 16.20 (1H, s, br)

d) 3-[[(4S)-4-Hydroxy-2-isoxazolidinyl]carbonyl]-5-methyl-7-(2-methylpropyl)-2-[(1,3,5-trimethylpyrazol-4-yl)methyl]-thieno[2,3-d]pyridazin-4(5H)-one Prepared from the product of part c) by the method of example 10 part e) to give the title compound as a solid.

MS (APCI) 460 [M+H]$^+$ $\delta\,^1H_{DMSO}$ 0.90 (6H, d), 2.00–2.14 (7H, m), 2.56 (2H, d), 3.48–4.16 (12H, m), 4.60–4.82 (1H, m), 5.50–5.60 (1H, m)

EXAMPLE 12

2-[[3,5-dimethyl-1-(2-pyridinyl)-1H-pyrazol-4-yl)methyl]-7-ethyl-3-[[(4S)-4-hydroxy-2-isoxazolidinyl]carbonyl]-5-methyl-thieno[2,3-d]pyridazin-4-(5H)-one

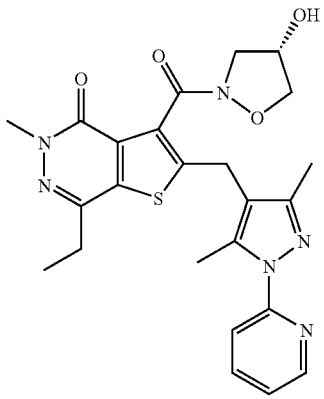

a) 2-Bromo-7-ethyl-5-methyl-thieno[2,3-d]pyridazin-4(5H)-one

Prepared from the product of example 3, part b) following the procedure of example 4, part d) to give the sub-title compound as a solid.

MS (ESI) 273 and 275 [M+H]$^+$ $\delta\ ^1H_{CDCl_3}$ 1.35 (3H, t), 2.77 (2H, q), 3.82 (3H, s), 7.70 (1H, s)

b) 3-(1,3-Dithian-2-ylidene)-2,4-pentanedione

To a solution of 2,4-pentanedione (10.5 ml) in dimethylformamide (200 ml) was added potassium carbonate (42.5 g) then carbon disulfide (9.3 ml). To the resulting mixture was added 1,3-dibromopropane, dropwise over 40 min. The mixture was stirred at ambient temperature under a nitrogen atmosphere for 20 hrs. then ice/water (200 ml) was added and the suspension was stirred for 1 hr. The solid was collected by filtration, washed with water and then recrystallised from ethanol to give the sub-title compound as a solid (23.3 g).

MS (ESI) 217 [M+H]$^+$ $\delta\ ^1H_{CDCl_3}$ 2.28 (2H, pentet), 2.34 (6H s), 2.95 (4H, t)

c) 3-(1,3-Dithian-2-yl)-2,4-pentanedione

To an ice-cooled suspension of the product of part b) (23.3 g) in dry methanol was added magnesium turnings (9.0 g) portionwise and the resulting mixture was stirred at ambient temperature under a nitrogen atmosphere for 18 hrs. The mixture was evaporated under reduced pressure, then water (500 ml) was added and the mixture was acidified to pH1 with concentrated hydrochloric acid with stirring. The aqueous mixture was extracted with dichloromethane (×2) and the combined organic extracts were dried over anhydrous magnesium sulfate, filtered and evaporated under reduced pressure. The residue was purified by column chromatography over silica; eluting with iso-hexane/ethyl acetate (9:1) and then recrystallised from isopropyl alcohol to give the sub-tide compound as a solid (4.0 g).

$\delta\ ^1H_{CDCl_3}$ 2.03 (2H, m), 2.25 (6H s), 2.78 (2H, m), 2.94 (2H, m), 4.32 (1H, d), 4.51 (1H, d)

d) 2-[4-(1,3-Dithian-2-yl)-3,5-dimethyl-1H-pyrazol-1-yl]-pyridine

Prepared from a solution of the product of part c) (2.8 g) and 2-pyridylhydrazine (1.55 g) in ethanol (20 ml) stirred at ambient temperature for 19 hrs and then heated to reflux for 1 hr. After evaporation the residue was purified by column chromatography over silica, eluting with iso-hexane/ethyl acetate (8:2) to give the sub-title compound as a solid (1.4 g).

MS (ESI) 292 [M+H]$^+$ $\delta\ ^1H_{CDCl_3}$ 1.92 (1H, s), 2.16 (1H, m), 2.44 (3H, s), 2.74 (3H, s), 2.88 (2H, dt), 3.06 (2H, m), 5.26 (1H, s), 7.17 (1H, m), 7.77 (2H, m), 8.42 (1H, m)

e) 3,5-Dimethyl-1-(2-pyridinyl)-1H-pyrazole-4-carboxaldehyde

Prepared from a solution of the product of part d) in acetonitrile (80 ml) and water (10 ml) with addition of N-bromosuccinimide (1.22 g) at 0° C. The resulting mixture was stirred for 1.5 hrs. then additional N-bromosuccinimide (0.5 g) was added and the mixture stirred for further 1.5 hrs. Further N-bromosuccinimide (0.2 g) was added and the mixture was stirred for a further 45 min. before quenching with sodium sulfite solution. The mixture was extracted with ethyl acetate and the organic solution was washed with water then brine, dried over anhydrous magnesium sulfate, filtered and evaporated under reduced pressure to give the sub-title compound as a solid.

MS (ESI) 202 [M+H]$^+$ $\delta\ ^1H_{DMSO}$ 2.43 (3H, s), 2.83 (3H, S), 7.46 (1H, m), 7.83 (1H, d), 8.04 (1H, td), 8.55 (1H, m), 10.10 (H, s)

f) 3-Bromo-2-[[3,5-dimethyl-1-(2-pyridinyl)-1H-pyrazol-4-yl]hydroxymethyl]-7-ethyl-5-methyl-thieno[2,3-d]pyridazin-4(5H)-one To a solution of the product of part a) (930 mg) in THF (10 ml) was added freshly prepared lithium diisopropylamide (1.6 ml n-butyl lithium in hexanes and 0.62 ml diisopropylamine in THF 10 ml) dropwise at −78° C. with stirring under nitrogen, and the resulting mixture was stirred for 20 min. A suspension of the product of part e) (705 mg) in THF (10 ml) was added dropwise and the mixture was allowed to warm to room temperature and stirred for 3 hr. It was poured into sodium bicarbonate solution and extracted with ethyl acetate (×3), the organic extracts were dried over anhydrous magnesium sulfate, filtered and evaporated under reduced pressure. The residue was triturated with ether to give the sub-title compound as a solid (800 mg).

MS (ESI) 474 and 476 [M+H]$^+$ $\delta\ ^1H_{DMSO}$ 1.28 (3H, t), 2.12 (3H, s), 2.63 (3H, s), 2.82 (2H, quartet), 3.66 (3H, s), 5.98 (1H, m), 6.67 (1H, m), 7.33 (1H, m), 7.76 (1H, m), 7.95 (1H, m), 8.46 (1H, m)

g) 3-Bromo-2-[[3,5-dimethyl-1-(2-pyridinyl)-1H-pyrazol-4-yl]methyl]-7-ethyl-5-methyl-thieno[2,3-d]pyridazin-4(5H)-one Prepared from the product of part f) following the procedure of example 1, part f) to give the sub-title compound as a solid.
MS (ESI) 458 and 460 [M+H]⁺
$\delta^1H_{DMSO}$ 1.19 (3H, t), 2.17 (3H, s), 2.59 (3H, s), 2.73 (2H, quartet), 3.67 (3H, s), 4.07 (2H, s), 7.35 (1H, m), 7.83 (1H, m), 7.96 (1H, m), 8.47 (1H, m)

h) 2-[[3,5-Dimethyl-1-(2-pyridinyl)-1H-pyrazol-4-yl]methyl]-7-ethyl-4,5-dihydro-5-methyl-4-oxo-thieno[2,3-d]pyridazine-3-carboxylic acid To a solution of the product of part g) (485 mg) in anhydrous THF (20 ml) was added 2M isopropyl magnesium chloride solution (0.58 ml) dropwise at 0–5° C. with stirring under nitrogen, and the resulting mixture was stirred at 0° C. for 30 min. It was quenched with a stream of carbon dioxide for 2.5 hr allowing the mixture to warm to room temperature. 2M hydrochloric acid was added and readjusted to pH3 with 1M sodium hydroxide solution. The aqueous mixture was extracted with ethyl acetate, the organic extracts dried over anhydrous magnesium sulfate, filtered and evaporated under reduced pressure. The residue was triturated with ether to give the subtitle compound as a solid (175 mg).
MS (ESI) 424 [M+H]⁺
$\delta^1H_{DMSO}$ 1.18 (3H, t), 2.15 (3H, s), 2.56 (3H, s), 2.82 (2H, quartet), 3.83 (3H, s), 4.51 (2H, s), 7.35 (1H, m), 7.85 (1H, m), 7.94 (1H, m), 8.48 (1H, m)

i) 2-[[3,5-Dimethyl-1-(2-pyridinyl)-1H-pyrazol-4-yl]methyl]-7-ethyl-3-[[(4S)-4-hydroxy-2-isoxazolidinyl]carbonyl]-5-methyl-thieno[2,3-d]pyridazin-4(5H)-one Prepared from the product of part h) following the procedure of example 5, part g) to give the title compound as a solid.
MS (ESI) 495 [M+H]⁺
$\delta^1H_{DMSO}$ 1.22 (3H, t), 2.15 (3H, s), 2.57 (3H, s), 2.66 (2H, m), 3.30 (3H, m), 3.49–4.18 (6H, m), 4.56–4.81 (1H, m), 5.52 (1H, m), 7.32 (1H, dt), 7.81 (1H, d), 7.96 (1H, dt), 8.45 (1H, d)

EXAMPLE 13

2-[[3,5-Dimethyl-1-(2-pyridinyl)-1H-pyrazol-4-yl]methyl]-7-ethyl-3-[[(4S)-4-hydroxy-4-methyl-2-isoxazolidinyl]carbonyl]-5-methyl-thieno[2,3-d]pyridazin-4(5H)-one

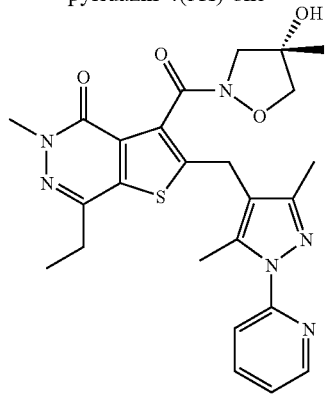

a) 2-[[3,5-Dimethyl-1-(2-pyridinyl)-1H-pyrazol-4-yl]methyl]-7-ethyl-3-[[(4S)-4-hydroxy-4-methyl-2-isoxazolidinyl]carbonyl]-5-methyl-thieno[2,3-d]pyridazin-4(5H)-one Prepared from the product of example 12 part h) following the procedure of example 6, part e) to give the title compound as a solid.
MS (ESI) 509 [M+H]⁺
$\delta^1H_{DMSO}$ 1.22 (3H, t), 1.33–1.44 (3H, m), 2.17 (3H, m), 2.57 (3H, s), 2.76 (2H, m), 3.56–4.10 (9H, m), 5.27–5.58 (1H, m), 7.35 (1H, m), 7.81 (1H, m), 794 (1H, m), 8.46 (1H, m)

EXAMPLE 14

7-Ethyl-3-{[(4S)-4-hydroxy-4-methylisoxazolidin-2-yl]carbonyl}-5-methyl-2-(1H-pyrrolo[2,3-b]pyridin-3-ylmethyl)thieno[2,3-d]pyridazin-4(5H)-one

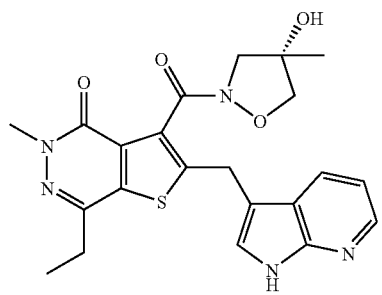

a) 2-Bromo-7-ethyl-5-methyl-thieno[2,3-d]pyridazin-4(5H)-one

Prepared from the product of example 3, part c) following the procedure of example 4, part d) to give the sub-title compound as a solid.
MS (ESI) 2731275 [M+H]⁺
$\delta^1H_{CDCl_3}$ 1.35 (3H, t), 2.77 (2H, q), 3.82 (3H, s), 7.70 (1H, s)

b) 3-Bromo-7-ethyl-2-{hydroxy[1-(phenylsulfonyl)-1H-pyrrolo[2,3-b]pyridin-3-yl]methyl}-5-methylthieno[2,3-d]pyridazin-4(5H)-one Prepared from the product of part a) following the procedure of example 10, part a) to give the sub-title compound as a solid.
MS (ESI) 559/561 [M+H]⁺
$\delta\alpha^1H_{DMSO}$ 1.16 (3H, t), 2.79 (2H, q), 3.65 (3H, s), 6.62 (1H, m), 7.06(1H, m), 7.33 (1H m), 7.62 (2H, m), 7.74 (1H, m), 7.84(1H, s), 8.02 (1H, dd), 8.10 (2H, m), 8.38 (1H, m)

c) 3-Bromo-7-ethyl-5-methyl-2-{[1-(phenylsulfonyl)-1H-pyrrolo[2,3-b]pyridin-3-yl]methyl}thieno[2,3-d]pyridazin-4(5H)-one Prepared from the product of part b) following the procedure of example 10, part b) to give the sub-title compound as a solid.
MS (ESI) 543/545 [M+H]⁺
$\delta^1H_{DMSO}$ 1.18 (3H, t), 2.65 (2H, q), 3.64 (3H, s), 4.42 (2H, s), 7.35 (1H, m), 7.61 (2H, m), 7.71 (1H, m), 7.95(1H, s), 7.98 (1H, dd), 8.07 (2H, m), 8.39 (1H, m)

d) 7-Ethyl-5-methyl-4-oxo-2-{[1-(phenylsulfonyl)-1H-pyrrolo[2,3-b]pyridin-3-yl]methyl}-4,5-dihydrothieno[2,3-d]pyridazine-3-carboxylic acid Prepared from the product of part c) following the procedure of example 10, part c) to give the sub-title compound as a solid.

MS (ESI) 509 [M+H]+

$\delta^1H_{DMSO}$ 1.25 (3H, m), 2.73 (2H, m), 3.71 (3H, s), 4.82 (2H, s), 7.26 (1H, m), 7.63 (3H, m), 7.74 (1H, m), 7.98 (1H, s), 8.04 (2H, m), 8.37 (1H, m)

e) 7-Ethyl-5-methyl-4-oxo-2-(1H-pyrrolo[2,3-b]pyridin-3-ylmethyl)-4,5-dihydrothieno[2,3-d]pyridazine-3-carboxylic acid A solution of the product of part d) (0.23 g) in methanol (10 ml) was treated with potassium hydroxide (76 mg) and heated under reflux for 3 hr. It was concentrated in vacuo, diluted with water and extracted with ethyl acetate (×2). The aqueous layer was acidified to pH5 using glacial acetic acid and extracted with ethyl acetate (×3). The combined organic extracts were dried over anhydrous magnesium sulfate, filtered and evaporated under reduced pressure to give the sub-title compound as a solid (0.064 g).

MS (ESI) 369 [M+H]+ f) 7-Ethyl-3-{[(4S)-4-hydroxy-4-methylisoxazolidin-2-yl]carbonyl}-5-methyl-2-(1H-pyrrolo[2,3-b]pyridin-3-ylmethyl)thieno[2,3-d]pyridazin-4(5H)-one To a solution of the product of part e) (0.08 g), and 1-hydroxybenzotriazole (0.037 g) in dimethylformamide (2 ml) was added triethylamine (0.135 ml) followed by diethyl chlorophosphate (0.035 ml) and the mixture was stirred at ambient temperature under nitrogen for 1.5 hr. (4S)-4-Methyl-4-isoxazolidinol hydrochloride (0.033 g) was added and the mixture was stirred at ambient temperature under nitrogen for 20 hr. It was diluted with saturated sodium bicarbonate solution and extracted with DCM (×3). The organic extracts were dried over anhydrous magnesium sulfate, filtered and evaporated under reduced pressure. The residue was purified by column chromatography over silica, eluting with DCM/methanol (98:2) followed by DCM/methanol (96:4) to give the title compound as a solid (0.05 g).

MS (ESI) 454 [M+H]+

$\delta^1H_{DMSO}$ 1.17 (3H, m), 1.32–1.46 (3H, m), 2.70 (2H, q), 3.65 (3H, m), 3.72–3.83 (4H, m), 4.36 (2H, m), 5.23–5.62 (1H, m), 7.02 (1H, m), 7.48 (1H, m), 7.92 (1, m), 8.20 (1H, dd), 11.58 (1H, bs)

EXAMPLE 15

2-[(3,5-Dimethyl-1-(2-pyridinyl)-1H-pyrazol-4-yl)methyl]-3-[[(4S)-4-hydroxy-4-methyl-2-isoxazolidinyl]carbonyl-5-methyl-7-(1-methylethyl)thieno[2,3-d]pyridazin-4(5H)-one

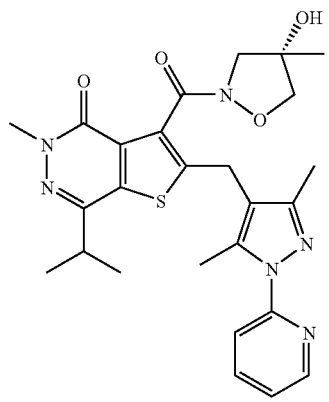

a) 3-Bromo-2-[[3,5-dimethyl-1-(2-pyridinyl)-1H-pyrazol-4-yl]hydroxymethyl]7-(1-methylethyl)-5-methyl-thieno[2,3-d]pyridazin-4(5H)-one Prepared from the product of example 1 part c) following the procedure of example 12, part f) to give the sub-title compound as a solid.

MS (APCI) 489 and 491 [M+H]+

$\delta^1H_{CDCl_3}$ 1.35 (6H, d), 2.35 (3H, s), 2.75 (1H, s), 2.87 (1H, bs), 3.07 (1H, m), 3.80 (3H, s), 6.21 (1H, s), 7.21 (1H, m), 8.78 (2H, m)

b) 3-Bromo-2-[[3,5-dimethyl-1-(2-pyridinyl)-1H-pyrazol-4-yl]methyl]-7-(1-methylethyl-5-methyl-thieno[2,3-d]pyridazin-4(5H)-one Prepared from the product of part a) following the procedure of example 1, part t) to give the sub-title compound as a solid.

MS (ESI) 472 and 474 [M+H]+

$\delta^1H_{CDCl_3}$ 1.28 (6H, d), 2.26 (3H, s), 2.62 (3H, s), 2.94 (1H, m), 3.81 (3H, s), 4.01 (2H, s), 7.19 (1H, m), 7.81 (1H, m), 7.88 (1H, dd), 8.44 (1H, m)

c) 2-[[3,5-Dimethyl-1-(2-pyridinyl)-1H-pyrazol-4-yl]methyl]-7-ethyl-4,5-dihydro-5-methyl-4-oxo-thieno[2,3-d]pyridazine-3-carboxylic acid Prepared from the product of part b) following the procedure of example 12, part h) to give the sub-title compound as a solid.

MS (ESI) 438 [M+H]+

$\delta^1H_{CDCl_3}$ 1.30 (6H, d), 2.23 (3H, s), 2.59 (3H, s), 3.05 (1H, m), 3.94 (3H, s), 4.64 (2H, s), 7.20 (1H, dd), 7.83 (1H, td), 7.91 (1H, d), 8.45 (1H, dd), 16.82 (1H, s)

d) 2-[(3,5-Dimethyl-1-(2-pyridinyl)-1H-pyrazol-4-yl)methyl]-3-[[(4S)-4-hydroxy-4-methyl-2-isoxazolidinyl]carbonyl-5-methyl-7-(1-methylethyl)thieno[2,3-d]pyridazin-4(5H)-one Prepared from the product of part c) following the procedure of example 5, part g) to give the title compound as a solid

MS (ESI) 523 [M+H]+

$\delta\,^1H_{CDC13}$ 1.31 (6H, m), 1.51 (3H, s), 2.27 (3H, s), 2.62 (3H, s), 3.00 (1H, m), 3.44 (1H, d), 3.79 (3H, s), 3.81 (1H, d), 3.97 (1H, d), 4.11 (2H, dd), 4.56 (1H, d), 6.13 (1H, s), 7.18 (1H, t), 7.82 (2H, m), 8.44 (1H, d)

EXAMPLE 16

2-[(3,5-Dimethyl-1-(2-pyrimidinyl)-1H-pyrazol-4-yl)methyl]-3-[[(4S)-4-hydroxy-4-methyl-2-isoxazolidinyl]carbonyl-5-methyl-7-(1-methylethyl)thieno[2,3,-d]pyridazin-4(5H)-one

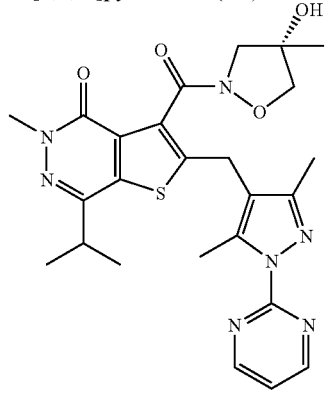

Prepared from the product of example 6 (0.9 g) and 2-bromopyrimidine (0.64 g) in acetonitrile (3 mL) heated in a microwave at 130° C. for 15 mins. After evaporation the residue was purified by column chromatography over silica, eluting with ethyl acetate/methanol (20:1) to give the title compound as a solid (0.032 g).

MS (ESI) 524 [M+H]+

$\delta\,^1H_{CDC13}$ 1.31 (6H, t), 1.52 (3H, s), 2.32 (3H, s), 2.66 (3H, s), 2.97 (1H, m), 3.40 (1H, d), 3.83 (1H, d), 3.98 (1H, d), 4.13 (2H, dd), 4.56 (1H, d), 6.12 (1H, b), 7.19 (1H, t), 8.77 (2H, d)

EXAMPLE 17

2-[(3,5-Dimethyl-1-(2-thiazolyl)-1H-pyrazol-4-yl)methyl]-3-[[(4S)-4-hydroxy-4-methyl-2-isoxazolidinyl]carbonyl-5-methyl-7-(1-methylethyl)thieno[2,3,-d]pyridazin-4(5H)-one

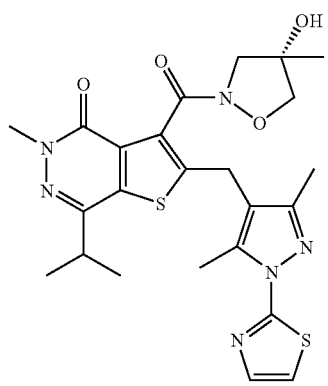

Prepared from the product of example 6 (0.222 g), 2-bromothiazole (0.222 g), copper (1) iodide (0.95 g) and trans diaminocyclohexane (0.06 mL) mixed under nitrogen. Potassium carbonate (0.22 g) and dry dioxan (2 mL) were added and the mixture heated at 110° C. for 3 days. After evaporation the residue was purified by column chromatography over silica, eluting with ethyl acetate/methanol (98:2) then preparative reverse phase HPLC using acetonitrile/aq. ammonia to give the title compound as a solid (0.023 g).

MS (ESI) 529 [M+H]+

$\delta\,^1H_{CDC13}$ 1.31 (6H, t), 1.51 (3H, s), 2.25 (3H, s), 2.67 (3H, s), 3.00 (1H, m), 3.41 (1H, d), 3.79 (3H, s), 3.80 (1H, d), 3.97 (1H, d), 4.09 (2H, dd), 4.55 (1H, d), 6.10 (1H, s), 7.06 (1H, d), 7.53 (1H, d)

Pharmacological Data

Inhibition of PMA/ionomycin-stimulated peripheral blood mononuclear cell proliferation The assay for PMA/ionomycin-stimulated PBMC proliferation was performed in 96-well flat-bottomed microtitre plates. Compounds were prepared as 10 mM stock solutions in dimethyl sulfoxide. A 50-fold dilution of this was prepared in RPMI and serial dilutions were prepared from this solution. 10 μl of the 50-fold diluted stock, or dilutions of it, were added to the well to give concentrations in the assay starting at 9.5 μM and going down. Into each well was placed 1×10⁵ PBMC, prepared from human peripheral blood from a single donor, in RPMI1640 medium supplemented with 10% human serum, 2 mM glutamine and penicillin/streptomycin. Phorbol myristate acetate (PMA) (0.5 ng/ml final concentration) and ionomycin (500 ng/ml final concentration) were added to these cells in supplemented RPMI1640 medium (as above) so that the final volume of the assay was 0.2 ml. The cells were incubated at 37° C. in a humidified atmosphere at 5% carbon dioxide for 72 hours. ³H-Thymidine (0.5 μCi) was added for the final 6 hours of the incubation. The level of radioactivity incorporated by the cells was then determined and this is a measure of proliferation.

The compounds of the Examples were found to exhibit an $IA_{50}$ value of less than $1\times10^{-6}$ M in the above test. Examples 3, 7 and 12 had a $PIA_{50}$ of 8.2, 7.6 and 8.8 respectively in the above test.

The invention claimed is:

1. A compound of formula (I):

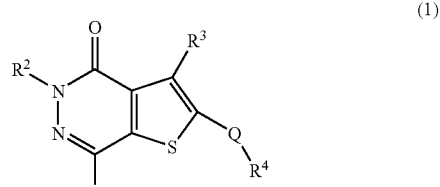

wherein:

$R^1$ is $C_{1-6}$ alkyl, $C_{2-6}$ alkenyl or $C_{3-6}$ cycloalkyl which is optionally substituted by $C_{1-6}$ alkyl, each of the above being optionally substituted by one or more halogen atoms;

$R^2$ is $C_{1-6}$ alkyl;

$R^3$ is a group CO—G or $SO_2$—G where G is a 5- or 6-membered ring containing a nitrogen atom and a second heteroatom selected from oxygen and sulphur adjacent to the nitrogen, and optionally substituted by up to 3 groups selected from hydroxyl and $C_{1-4}$ alkyl;

Q is CR⁵R⁶ where R⁵ is hydrogen, $C_{1-6}$ alkyl or fluorine and R⁶ is hydrogen, OH or fluorine, or R⁵ and R⁶ together form a =O group, with the proviso that R⁵ cannot be fluorine when R⁶ is OH;

R⁴ is a 5- to 10-membered mono- or bi-cyclic aromatic ring system, containing 0 to 4 heteroatoms independently selected from nitrogen, oxygen and sulphur, the ring system being optionally substituted by up to 4 groups independently selected from halogen, $C_{1-4}$ alkyl, (poly)halo-$C_{1-4}$-alkyl, $C_{1-4}$ alkoxy, (poly)halo-$C_{1-4}$-alkoxy, $C_{1-4}$ alkylsulphonyl, (poly)halo-$C_{1-4}$-alkylsulphonyl, oxo, thioxo, cyano, hydroxymethyl, methylthio, —NR⁷R⁸, —CO—NR⁷R⁸, —SO₂NR⁷R⁸, or a 5- to 6-membered aromatic ring system wherein up to 3 ring atoms may be heteroatoms independently selected from oxygen, sulphur and nitrogen, and which may itself be substituted by up to 4 groups selected from halogen, $C_{1-4}$ alkyl, (poly)halo-$C_{1-4}$-alkyl, $C_{1-4}$ alkoxy, (poly)halo-$C_{1-4}$-alkoxy, $C_{1-4}$ alkylsulphonyl, (poly)halo-$C_{1-4}$-alkylsulphonyl, oxo, thioxo, cyano, hydroxymethyl, methylthio, —NR⁷R⁸, —CO—NR⁷R⁸, and —SO₂—NR⁷R⁸;

R⁷ and R⁸ are independently hydrogen, or $C_{1-4}$ alkyl; or R⁷ and R⁸ together with the nitrogen atom to which they are attached may form a 5 to 7 membered saturated heterocyclic ring, and pharmaceutically acceptable salts and solvates thereof.

2. A compound according to claim 1 in which R¹ is $C_{1-6}$ alkyl or $C_{3-6}$ cycloakyl.

3. A compound according to claim 1 in which R² is methyl.

4. A compound according to claim 1 in which R is a group CO—G.

5. A compound according to claim 1 in which Q is CH₂.

6. A compound according to claim 1 in which R⁴ is a 5 membered aromatic ring containing two heteroatoms optionally substituted as defined in claim 1.

7. A compound according to claim 6 wherein R⁴ is a group of sub-formula (i)

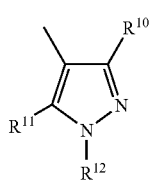

(i)

where R¹⁰ and R¹¹ are independently selected from H, $C_{1-6}$alkyl, or halo$C_{1-6}$alkyl;

and R¹² is selected from H, $C_{1-6}$alkyl, or halo$C_{1-6}$alkyl or a 5- to 6-membered aromatic ring system wherein up to 3 ring atoms may be heteroatoms independently selected from oxygen, sulphur and nitrogen.

8. A compound according to claim 7 wherein R¹⁰ and R¹¹ are methyl.

9. A compound according to claim 1 selected from:

2-[(3,5-dimethyl-1H-pyrazol-4-yl)methyl]-3-[[(4S)-4-hydroxy-2-isoxazolidinyl]carbonyl]-5-methyl-7-(1-methylethyl)thieno[2,3,-d]pyridazin-4(5H)-one, 2-[(3,5-Dimethyl-1H-pyrazol-4-yl)methyl]-3-[[(4S)-4-hydroxy-2-isoxazolidinyl]carbonyl]-5-methyl-7-(2-methylpropyl)thieno[2,3-d]pyridazin-4(5H)-one, 2-[(3,5-dimethyl-1H-pyrazol-4-yl)methyl]-7-ethyl-3-[[(4S)-4-hydroxy-2-isoxazolidinyl]carbonyl]-5-methyl-thieno[2,3-d]pyridazin-4(5H)-one, 7-Cycloprpyl-2[(3,5-dimethyl-1H-pyrazol-4-yl)methyl]-3-[[(4S)-4-hydroxy-2-isoxazolidinyl]carbonyl]-5-methyl-thieno[2,3-d]pyridazin-4(5H)-one, 7-Cyclopropyl-2-[(3,5-dimethyl-1H-pyrazol-4-yl)methyl]-5-ethyl-3-[[(4S)-4-hydroxy-2-isoxazolidinyl]carbonyl]-thieno[2,3-d]pyridazin-4(5H)-one, 2-[(3,5-Dimethyl-1H-pyrazol-4-yl)methyl]-3-[[(4S)-4-methyl-2-isoxazolidinyl]carbonyl-5-methyl-7-(1-methylethyl)thieno[2,3,-d]pyridazin-4(5H)-one, 2-[(3,5-Dimethyl-1H-pyrazol-4-yl)methyl]-3-[[(4S)-4-hydroxy-4-methyl-2-isoxazolidinyl]carbonyl]-5-methyl-7-(2-methylpropyl)-thieno[2,3,-d]pyridazin-4(5H)-one, 2-[(3,5-Dimethyl-1H-pyrazol-40yl)methyl]-7-ethyl-3-[[(4S)-4-hydroxy-4-methyl-2-isoxazolidinyl]carbonyl]-5-methyl-thieno[2,3-d]pyridazin-4(5H)-one, 7-Cyclopropyl-2-[(3,5-dimethyl-1H-pyrazol-4-yl)methyl]-3-[[(4S)-4-hydroxy-4-methyl-2-isoxazolidinyl]carbonyl]-5-methyl-thieno[2,3-d]pyridazin-4(5H)-one, 3-[[(4S)-4-hydroxyisoxazolidinyl]carbonyl-5-methyl-7-(2-methylpropyl)-2-(1H-pyrrolo[2,3-b]pyridine-3-ylmethyl)thieno[2,3,-d]pyridazin-4(5H)-one, 3-[[(4S)-4-Hydroxy-2-isoxazolidinyl]carbonyl]-5-methyl-7-(2-methylpropyl)-2-[(1,3,5-trimethylpyrazol-4-yl)methyl]-thieno[2,3,-d]pyridazin-4(5H)-one, 2-[[3,5-dimethyl-1-(2-pyridinyl)-1H-pyrazol-4-yl]methyl]-7-ethyl-3-[[(4S)-4-hydroxy-2-isoxazolidinyl]carbonyl]-5-methyl-thieno[2,3-d]pyridazin-4(5H)-one, 2-[[3,5-Dimethyl-1-(2-pyridinyl)-1H-pyrazol-4-yl]methyl]-7-ethyl-3-[[(4S)-4-hydroxy-4-methyl-2-isoxazolidinyl]carbonyl]-5-methyl-thieno[2,3-d]pyridazin-4(5H)-one, 7-Ethyl-3-{[(4S)-4-hydroxy-4-methylisoxazolidin-2-yl]carbonyl}-5-methyl-2-(1H-pyrrolo[2,3-b]pyridin-3-ylmethyl)thieno[2,3-d]pyridazin-4(5H)-one, 2-[(3,5-Dimethyl-1-(2-pyridinyl)-1H-pyrazol-4-yl)methyl]-3-[[(4S)-4-hydroxy-4-methyl-2-isoxazolidinyl]carbonyl-5-methyl-7-(1-methylethyl)thieno[2,3,-d]pyridazin-4(5H)-one, 2-[(3,5-Dimethyl-1-(2-pyrimidinyl)-1H-pyrazol-4-yl)methyl]-3-[[(4S)-4-hydroxy-4-methyl-2-isoxazolidinyl]carbonyl-5-methyl-7-(1-methylethyl)thieno[2,3,-d]pyridazin-4(5H)-one, 2-[(3,5-Dimethyl-1-(2-thiazolyl)-1H-pyrazol-4-yl)methyl]-3-[[(4S)-4-hydroxy-4-methyl-2-isoxazolidinyl]carbonyl-5-methyl-7-(1-methylethyl)thieno[2,3,-d]pyridazin-4(5H)-one and pharmaceutically acceptable salts thereof.

10. A pharmaceutical composition comprising a compound of formula (I) or a pharmaceutically acceptable salt thereof as defined in claim 1 in association with a pharmaceutical carrier.

11. A process for the preparation of a compound of formula (I) which comprises:

(a) for compounds of formula (I) where R³ is COG: reaction of a compound of formula (II):

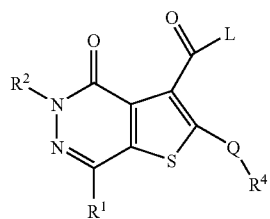

(II)

in which R¹, R², R⁴ and Q are as defined in formula (I) or are protected derivatives thereof, with a compound of formula (III):

G—H    (III)

where G is as defined in formula (I) in the presence of a coupling agent, or (b) for compounds of formula (I) where R³ is SO₂—G: reacting a compound of formula (IV):

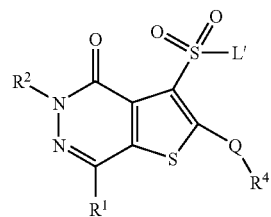

(IV)

in which in which R¹, R², R⁴ and Q are as defined in formula (II) and L and L' are leaving group, with a compound of formula (III) as defined above, and optionally thereafter process (a) or (b) in any order removing any protecting groups, forming a pharmaceutically acceptable salt.

* * * * *